Figure 1:
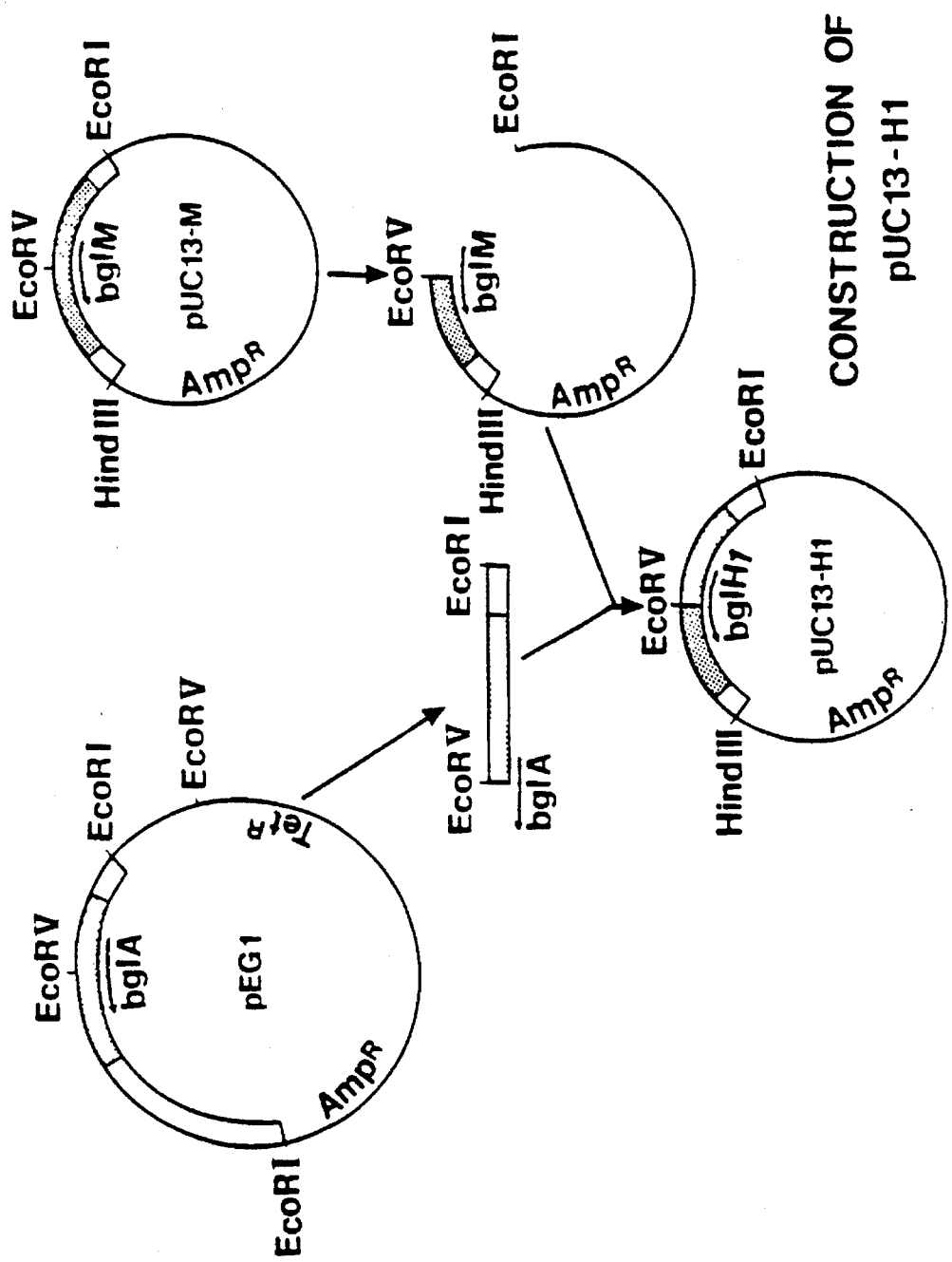

United States Patent [19]

Borriss et al.

[11] Patent Number: 5,470,725

[45] Date of Patent: Nov. 28, 1995

[54] THERMOSTABLE (1,3-1,4)-β-GLUCANASE

[75] Inventors: Rainer Borriss, Berlin; Jürgen Hofemeister, Gatersleben, both of Germany; Karl K. Thomsen, Slagelse, Denmark; Ole Olsen, Copenhagen, Denmark; Dietrich Von Wettstein, Værløse, Denmark

[73] Assignees: Carlsberg A/S, Copenhagen, Denmark; Akademie der Wissenschaften der DDR, Berlin, Germany

[21] Appl. No.: 103,998

[22] Filed: Aug. 10, 1993

Related U.S. Application Data

[63] Continuation of Ser. No. 773,652, filed as PCT/DK90/00044, Feb. 16, 1990, abandoned.

[30] Foreign Application Priority Data

Feb. 16, 1989 [DD] German Dem. Rep. ............. 325 8000
Aug. 4, 1989 [DK] Denmark ................................ 3848/89

[51] Int. Cl.$^6$ .............................. C12P 19/02; C12N 9/24; C12N 15/56
[52] U.S. Cl. .................... 435/93; 435/105; 435/200; 435/240.1; 435/243; 435/252.33; 435/254.21; 536/23.2
[58] Field of Search ................................ 435/200, 240.1, 435/243, 252.8, 93, 105, 252.33, 254.21; 536/23.2; 426/16, 52, 53

[56] References Cited

FOREIGN PATENT DOCUMENTS 0252666 1/1988 European Pat. Off. .
272102 9/1989 Germany .

OTHER PUBLICATIONS

Politz, O., et al., (1993) Eur. J. Biochem 216, 829–834.
Argos et al. "Thermal Stability and Protein Structure", *Biochemistry*, 18:5698–5703 (1979).
Bolivar et al. "Construction and characterization of new cloning vehicle. II. A multipurpose cloning system," *Gene* 2:95–113 (1977).
Borriss "Purification and characterization of an extracellular beta–glucanase from *Bacillus* IMET B376[1])", *Z. Alg. Mikrobiologie* 21:7–17 (1981).
Borriss et al. "β–1,3–1,4–glucanase in sporeforming microorganisms. V. The efficiency of β–glucanase in reducing the viscosity of wort" *Zbl. Bakt II Abt.* 136:324–329 (1981).
Borriss et al. "Expression in *Escherichia coli* of a cloned β–glucanase gene from *Bacillus Amyloliquefaciens*" *Appl. Microbiol. Biotechnol.* 22:63–71 (1985).
Borriss et al. "Molecular cloning of a gene coding for thermostable beta–glucanase from *Bacillus macerans*" *J. Basic Microbiol.* 28:3–10 (1988).
Bradford "A rapid and sensitive method for the quantitation of microgram quantities of protein utilizing the principle of protein dye binding" *Anal. Biochem.* 72:248–254 (1976).
Cantwell et al. "Molecular cloning and expression of a *Bacillus subtilis* β–glucanase gene in *Escherichia coli*" *Gene* 23:211–219 (1983).

Godfrey "On comparison of key characteristics of industrial enzymes by type and source," *Industrial Enzymology*, 5:466–569 (1983).
Hanahan "Techniques for transformation of *E. coli*" DNA Cloning, vol. 1, A practical approach., 6:109–135 (1985).
Hattori et al. "Dideoxy sequencing method using denatured plasmid templates" *Anal. Chem.* 152:232–238 (1986).
Hofemeister "The β–glucanase gene from *Bacillus amyloliquefaciens* shows extensive homology with that of *Bacillus subtilis*" *Gene* 49:177–187 (1986).
Horton et al. "Engineering hybrid genes with the use of restriction enzymes: Gene splicing by overlap extension" *Gene* 77:61–68 (1989).
Imanaka et al. "A new way of enhancing the thermostability of proteases" *Nature*, 324:695–697 (1986).
Jorgensen "Quantification of high molecular weight (1–3 (1–4)–β–D–glucan using calcofluor complex formation and flow injection analysis. I. Analytical principle and its standardization" *Carlsberg Res. Commun.* 53:277–285 (1988).
Jorgensen et al. "Quantification of high molecular weight (1–3)(1–4)–β–D–glucan using calcofluor complex formation and flow injection analysis. II. Determination of total β–glucan content of barley and malt," *Carlsberg Res. Commun.* 53 287–296 (1988).
Laemmli "Cleavage of structural proteins during the assembly of the head of bacteriophage T4" *Nature* 227:680–685 (1970).
Lederberg et al. "Transformation of *Salmonella typhimurium* by plasmid deoxyribonucleic acid" *J. Bacteriol.* 119:1072–1074 (1974).
Loi et al. "Survival of barley (1–3,1–4)β–D–glucanase isoenzymes during kilning and mashing" *J. Cereal Sci.* 5:45–50 (1987).
Matthews et al. "Enhanced protein thermostability from site–directed mutations that decrease the entropy of unfolding" *Proc. Natl. Acad. Sci.* 84:6663–6667 (1987).
McCleary "Soluble, dye–labeled polysaccharides for the assay of endohydrolases" *Methods Enzymol.* 160:74–86 (1988).
McFadden et al. "Expression sites and developmental regulation of genes encoding (1–3,1–4)–β–D–glucanases in germinated barley" *Planta* 173:500–508 (1988).

(List continued on next page.)

Primary Examiner—Charles L. Patterson, Jr.
Attorney, Agent, or Firm—Foley & Lardner

[57] ABSTRACT

Novel hybrid thermostable (1,3-1,4)-β-glucanases, their use in food manufacturing and feed manufacturing, DNA fragments encoding such glucanases, organisms expressing the DNA fragments and a method for producing the thermostable (1,3-1,4)-β-glucanases. Hybrid fusion genes encoding Bacillus (1,3-1,4)-β-glucanases were constructed, the gene products of which are more thermostable than any (1,3-1,4)-β-glucanase known until now. The hybrid genes were constructed by reciprocal exchanges of the amino-terminal and carboxy-terminal parts of the β-glucanase encoding genes from *Bacillus amyloliquefaciens* and *Bacillus macerans*. The resulting thermostable (1,3-1,4)-β-glucanases retain a significant enzymatic activity at temperatures exceeding 65° C. and at pH values below 5.0.

72 Claims, 15 Drawing Sheets

OTHER PUBLICATIONS

Mead et al. "Single-stranded DNA 'blue' T7 promoter plasmids: A versatile tandem promoter system for cloning and protein engineering" *Protein Engineering* 1:67–74 (1986).

Merrifield "Solid phase peptide synthesis. I. The synthesis of a tetrapetide" *J. Am. Chem. Soc. 85:2149 (1963).*

Miller "Use of dinitrosalicylic acid reagent for determination of reducing sugars" *Analytical Chemistry* 31:426–428 (1959).

Murphy "The DNA sequence of the gene and genetic control sites for the excreted *B. subtilis* enzyme β–glucanase" *Nucleic Acids Res.* 12:5355–5367 (1984).

Querol "Tentative rules for increasing the thermostability of enzymes by protein engineering" *Enzyme Microb. Technol.* 9:238–244 (1987).

Shinnick et al. "Synthetic peptide immunogens as vaccines" *Ann. Rev. Microbiol.* 37:425–446 (1983).

Streuli et al. "Target cell specificity of two species of human interferon–alpha produced in *Escherichia coli* and of hybrid molecules derived from them" *Prod. Natl. Acad. Sci. USA* 78:2848–2852 (1981).

Thomsen "Mouse α–amylase synthesized by *Saccharomyces cerevisiae* is released into the culture medium" *Carlsberg Res. Comm.* 48:545–555 (1983).

Yanisch–Perron "Improved M13 phage cloning vectors and host strains: nucleotide sequences of the M13 mp18 and pUC19 vectors" *Gene* 33:103–119 (1985).

Weck et al. "Antiviral activities of hybrids of two major human leukocyte interferons" *Nucleic Acids Res.* 9:6153–6165 (1981).

Yon et al. "Precise gene fusion by PCR" *Nucleic Acids Res.* 17:4895 (1989).

Zhang et al. "Double stranded sequencing as a choice for DNA sequencing"*Nucleic Acids Res.* 16:1220 (1988).

Honda et al. "Cloning and expression in *Escherichia coli* of a *Thermoanaerobacter cellulolyticus* gene coding for heat–stable β–glucanase" *Appl Microbiol. Biotechnol.* 25:480–483 (1987).

Petre et al. "Purification and properties of an endo–β–1, 4–glucanase from *Clostridium thermocellum*", (abst.) 7–Enzymes 95:145879q (1981), *Biochemie* 63:629–639 (1981).

Tikhomirov et al. "Endo–1,4–β–glucanases of the anaerobic bacterium *Clostridium thermocellum* st. No. 3 with high heat stability" *Chemical Abstracts* 110:168879g (1989).

Schwarz et al. "Isolation of a *Clostridium thermocellum* gene encoding a thermostable β–1,3–glucanase (laminarinase)" *Chemical Abstracts* 108:217067k (1988), *Biotechnology Letters* 10(4):225–230 (1988).

Klyosov et al. "A thermostable endo–1,4–β–glucanase from *Myceliophtora thermophilia*" *Chemical Abstracts* 109:50624w (1988).

HYBRID GENE ENCODING (1-3,1-4)-β-GLUCANASE H1

HYBRID GENE ENCODING (1-3,1-4)-β-GLUCANASE H2

THERMOSTABLE (1,3-1,4)-β-GLUCANASE

This application is a continuation of application Ser. No. 07/773,652, filed as PCT/DK90/00044, Feb. 16, 1990, now abandoned.

FIELD OF INVENTION

The present invention relates to novel thermostable (1,3-1,4)-β-glucanases, the use of novel thermostable (1,3-1,4)-β-glucanases, DNA fragments encoding such glucanases, organisms expressing the DNA fragments and a method for producing the thermostable (1,3-1,4)-β-glucanases.

TECHNICAL BACKGROUND (1,3-1,4)-β-glucanases are used in the manufacture of different food products and animal feed and as subsidiary materials in biological research when it is necessary to cleave the β-glycosidic linkages in (1,3-1,4)-β-glucans. Especially in the brewing industry the use of such glucan hydrolyzing enzymes permits the application of larger proportions of raw grain in substitution for the use of malt, without this causing any trouble in the filtration due to high viscosity of the mash which may be caused by an increased amount of glucan compounds.

The mixed linked (1,3-1,4)-β-glucans constitute the major part of the endosperm cell walls of cereals like oat and barley. They may cause severe problems in the brewing industry such as reduced yield of extract and lowered rates of wort separation or beer filtration. Remaining β-glucans in the finished beer may lead to the formation of hazes and gelatinous precipitates (Godfrey, 1983). Barley (1,3-1,4)-β-glucanases (EC 3.2.1.73) are synthesized in the scutellum and the aleurone layer during the early stages of germination of seeds (McFadden et al., 1988). However, a large proportion of the malt β-glucanase is irreversibly heat inactivated during kilning and the remaining activity is rapidly destroyed during mashing (Loi et al., 1987).

It has long been known that the viscosity of the wort can be reduced by using β-glucanases from mesophilic Bacillus strains, e.g. from *Bacillus amyloliquefaciens* or *Bacillus subtilis*. A serious disadvantage with the known glucanases is their temperature sensitivity, which implies that they are only effective during the early phase of the mashing process. Later on when temperatures are above 65° C. their activity is reduced substantially.

In an attempt to obtain a more thermostable glucanase, the gene from *Bacillus macerans* encoding glucanase was introduced into *Bacillus subtilis* in order to express the gene in this organism (DD Patent Application WP C12N/315 706 1). However, at 70° C. this glucanase is also rapidly and irreversibly denatured. Another drawback to the known glucanases in relation to the brewing process is that these glucanases do not exert their full activity in the pH range from 4 to 5 which is the normal condition during mashing. For example the activity of the Bacillus β-glucanase at pH 4.6 is only 20% of that between 6 and 7. Furthermore, the stability is reduced when the glucanase is incubated at pH 4.

The best characterized bacterial (1,3-1,4)-β-glucanases are those from *Bacillus subtilis* and *B. amyloliquefaciens* where the genes encoding the enzymes have been cloned and sequenced (Borriss et al., 1985; Cantwell and McConnell, 1983: Hofemeister et al., 1986; Murphy et al., 1984). It has recently been shown that the β-glucanase from *B. macerans* is more thermostable than the *B. subtilis* and *B. amyloliquefaciens* enzymes (Borriss, 1981; Borriss and Schroeder, 1981). However, at temperatures exceeding 65° C. and at pH values of 4.5 to 5.5, which is typical for industrial mashing, the *B. macerans* β-glucanase is rapidly inactivated. The *B. macerans* β-glucanase gene has been cloned (Borriss et al., 1988) and its nucleotide sequence determined (Borriss et al., in prep.). Comparison of the derived amino acid sequence of *B. macerans* β-glucanase with the derived sequences of *B. subtilis* and *B. amyloliquefaciens* β-glucanases reveals an overall homology of 70%.

During recent years a number of attempts have been made to construct improved forms of existing, biologically active proteins to make them better suited for industrial processes and to widen their range of application. Much interest has been focused on increasing the thermostability of enzymes. It has been proposed that the thermostability of enzymes may be enhanced by single amino acid substitutions that decrease the entropy of unfolding (Matthews et al., 1987). Several tentative rules for increasing the thermostability of proteins have been established (Argos et al., 1979; Imanaka et al., 1986; Querol and Parilla, 1987) but precise predictions for changes of function as a consequence of changes in structure remain elusive.

Several researchers have conducted experiments with in vitro recombination of homologous genes giving rise to hybrid proteins retaining the biological activity of the parental molecules. Streuli et al. (1981) as well as Weck and coworkers (1981) constructed hybrid human leukocyte interferon genes. Some of the hybrid interferons extended the host cell range for protection against Vesicular Stomatitis and Encephalomyocarditis virus. Thus the AD hybrids combining portions of interferons A and D elicited significantly higher antiviral activities than either parental molecule in mouse L-929 cells, human He-La cells and primary rabbit kidney cells. Heat stability, pH stability and antigenic specificity were the same for the hybrid and parental interferon molecules.

Danish Patent Application 3368/87 discloses the combination of DNA sequences from the *Bacillus licheniformis* and *Bacillus amyloliquefaciens* α-amylase genes in order to obtain a chimeric α-amylase enzyme for the liquefaction of starch, which did not have a negative effect on the maximum percentage by weight of dextrose obtainable by saccharification with a glycoamylase. This negative effect was reduced with the chimeric α-amylase and the thermostable properties were retained in comparison with the parent enzymes.

DISCLOSURE OF THE INVENTION

The present invention relates to a thermostable (1,3-1,4)-β-glucanase which retains at least 50% of its activity after 10 minutes, preferably 15 minutes, more preferably 18 minutes of incubation in 10 mM $CaCl_2$, 40 mM Na-acetate at pH 6.0 and 70° C., the incubated solution having a concentration range from 0.3 to 1 mg (1,3-1,4)-β-glucanase per ml, the activity of the (1,3-1,4)-β-glucanase being understood as the ability of the enzyme to hydrolyze β-glycosidic linkages in (1,3-1,4)-β-glucans.

In the present context, the term "thermostable" relates to the ability of an enzyme to resist denaturing and to retain the enzymatic activity at high temperatures for a period of time sufficient for the enzyme to convert its substrate into the reaction products, in the present case to cleave β-glycosidic linkages in (1,3-1,4)-β-glucans to obtain reducing sugars. By high temperatures is meant temperatures above 60° C.

Figure 10:
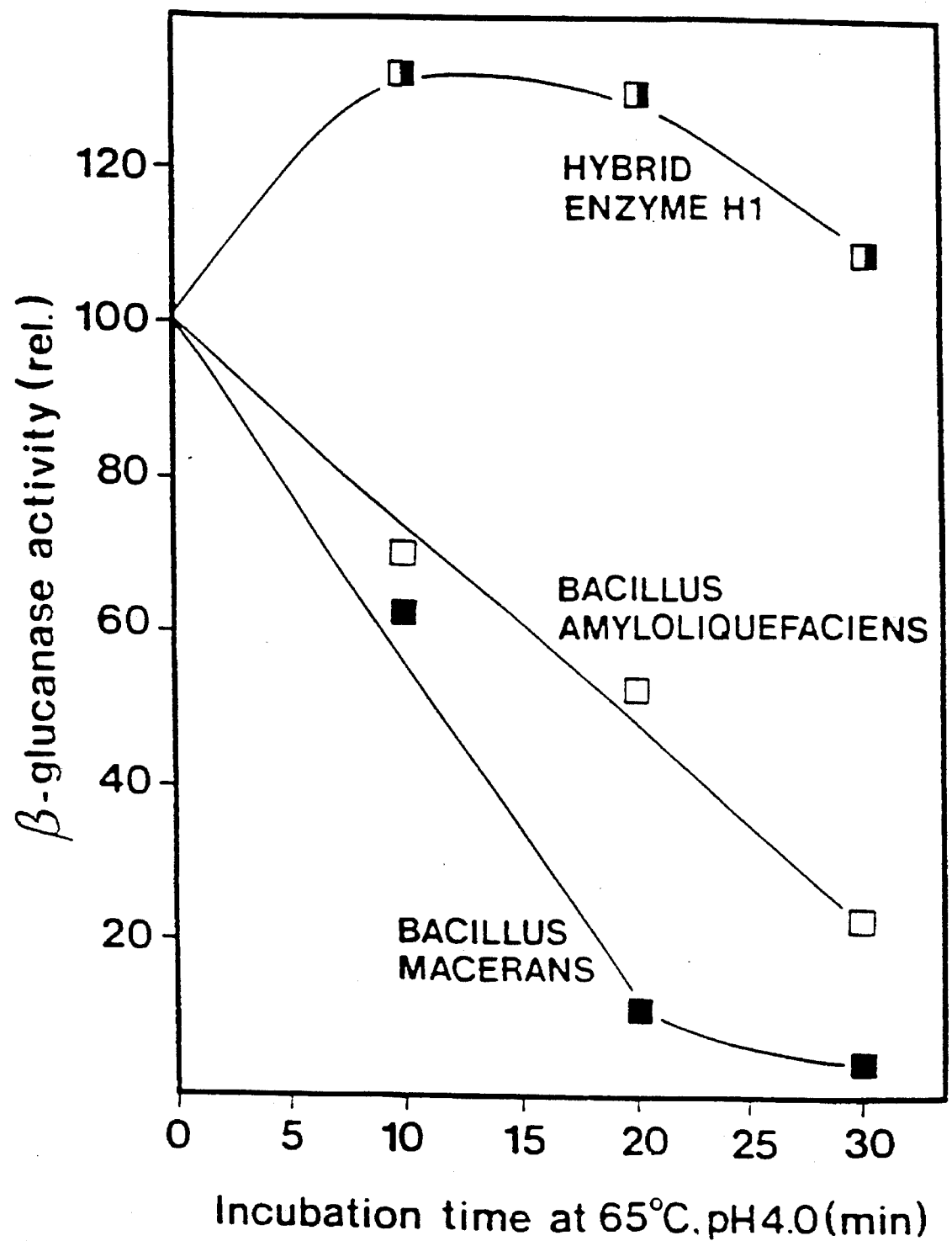

In another aspect, the present invention relates to a thermostable (1,3-1,4)-β-glucanase which after 10 minutes of incubation in crude cell extracts at 65° C. and pH 4.0 has a relative β-glucanase activity of at least 100%, preferably at least 110%, more preferably at least 120%. An example of such a characteristic behaviour of the (1,3-1,4)-β -glucanase of the invention is shown in FIG. 10, where the relative β-glucanase activity of hybrid enzyme H1 is compared to the relative β-glucanase activities of *B. amyloliquefaciens* and *B. macerans* β-glucanases. From FIG. 10 it is clear that the relative β-glucanase activity of the H1 enzyme is about 130% after 10 minutes of incubation.

The present inventors have constructed hybrid genes encoding recombinant Bacillus(1,3-1,4)-β-glucanases, which are more thermostable than any (1,3-1,4)-β-glucanases known until now. The hybrid genes were constructed by reciprocal exchanges of the amino-terminal and carboxyterminal parts of the β-glucanase encoding genes from *Bacillus amyloliquefaciens* and *Bacillus macerans* by using a common EcoRV endonuclease restriction site in the middle of the (1,3-1,4)-β-glucanase gene in *B. amyloliquefaciens* and *B. macerans*, respectively, as a fusion point or by construction of hybrid fusion genes using the polymerase chain reaction (PCR) according to Yon & Fried (Nucleic Acid Research, 1989, 17, 4895) and Horton et al. (Gene, 1989, 77, 61–68.

The β-glucanase hybrid enzyme 1 (H1) contains the 107 amino-terminal residues of mature *B. amyloliquefaciens* β-glucanase and the 107 carboxyl-terminal amino acid residues of *B. macerans* β-glucanase. A reciprocal β-glucanase hybrid enzyme 2 (H2) consists of the 105 amino-terminal parts from the *B. macerans* enzyme and the carboxylterminal 107 amino acids from *B. amyloliquefaciens*. The biochemical properties of the two hybrid enzymes differ significantly from each other as well as from both parental β-glucanases.

The hybrid enzymes H3, H4, H5, and H6 were constructed by using PCR. H3 contains the 16 amino-terminal amino acid residues of mature *B. amyloliquefaciens* (1,3-1,4)-β-glucanase and the 198 carboxy-terminal amino acid residues of *B. macerans* β-glucanase; H4 contains the 36 amino-terminal amino acid residues of mature *B. amyloliquefaciens* β -glucanase and the 178 carboxy-terminal residues of *B. macerans;* H5 contains the 78 amino-terminal amino acid residues of mature *B. amyloliquefaciens* (1,3-1, 4)-β-glucanase and the 136 carboxy-terminal amino acid residues of mature *B. macerans* β-glucanase; and H6 contains the 152 amino-terminal residues of mature *B. amyloliquefaciens* β-glucanase and the 62 carboxy-terminal amino acid residues of mature *B. macerans* (1,3-1,4)-β-glucanase.

Compared to the parental enzymes, the hybrid proteins exhibit novel biochemical properties such as different pH-optima, thermostability and differences in pH tolerance. The H1 protein is of special interest for the brewing industry since in this protein the tolerance to lower pH and a low pH optimum of enzymatic activity has been combined with a thermostability exceeding that of the *B. macerans* β-glucanase at high pH. The pH optimum and especially the pH tolerance has been shifted to more acidic conditions and the thermostability surpasses that of both parental enzymes over the entire tested pH range.

However, the properties of the thermostable (1,3-1,4)-β-glucanase of the invention also makes it interesting to use the enzyme for different purposes where it is desirable to obtain (1,3-1,4)-β-glucanase enzymatic activity at high temperature and possibly at low pH, e.g. in the manufacturing of coffee surrogates or feed pellets, especially for use in feeding poultry. Poultry are not able to degrade β-glucans in the feed and pelleted feed containing high amounts of β-glucans caused reduced feed/weight gain ratios and also digestive disorders.

Therefore, it is advantageous to degrade the β-glucans in the feed by adding (1,3-1,4)-β-glucanases to the feed. Production of the feed pellets takes place at high temperatures meaning that non-thermostable (1,3-1,4)-β-glucanases are rapidly degraded. However, this problem can now be solved by using the thermostable (1,3-1,4)-β-glucanase of the invention in the production.

Different strategies may be followed in the construction of a hybrid gene encoding a thermostable (1,3-1,4)-β-glucanase. Other restriction sties in the (1,3-1,4)-β-glucanase gene may be used; the nucleotide sequence of the (1,3-1, 4)-β-glucanase gene may be digested by nuclease followed by the introduction of synthetic nucleotide sequences containing useful endonuclease restriction sites; or a total or partially synthetic gene may be constructed. Also, (1,3-1, 4)-β-glucanase genes originating from other organisms than *B. amyloliquefaciens* and *B. macerans* may be used in order to obtain a hybrid gene encoding a thermostable (1,3-1,4)-β-glucanase.

Thus, in another aspect the present invention relates to a thermostable hybrid (1,3-1,4)-β-glucanase comprising an amino acid sequence with the formula

A–M where A is a polypeptide consisting of 5–200 amino acids which are at least 75%, preferably at least 85%, more preferably at least 90% identical to the amino acid residues of the N-terminal part of the *Bacillus amyloliquefaciens* or *Bacillus macerans* (1,3-1,4)-β-glucanase as given in Table I and M is a polypeptide consisting of 5 to 200 amino acids which are at least 75%, preferably at least 85%, more preferably at least 90% identical to the amino acid residues of the carboxy-terminal part of the *Bacillus macerans* or *Bacillus amyloliquefaciens* (1,3-1,4)-β-glucanase as shown in Table I.

The term "identical to" refers to a comparison of the overall composition of amino acids in two polypeptides or parts thereof. In each polypeptide the number of individual amino acid residues as well as the total number of amino acid residues is determined. Then, the degree of identity is given by the ratio of the number of identical amino acid residues in the two polypeptides relative to the total number of amino acid residues in the polypeptide to be compared. Thus, in the present context, the degree of identity is determined as the percentage of the amino acids in the (1,3-1,4)-β-glucanase of the invention or part thereof, which are identical to the amino acids in another polypeptide or part thereof, in the present case the amino-terminal part of *B. amyloliquefaciens* or *B. macerans* (1,3-1,4)-β -glucanase as given in Table I and the carboxy-terminal part of *B. macerans* or *B. amyloliquefaciens* (1,3-1,4)-β-glucanase as given in Table I, relative to the total number of amino acid residues in the compared part of (1,3-1,4)-β-glucanase. It should be recognized that identity is not dependent on the position of amino acids in the polypeptides and is absolute in the sense that identity is not related to possible homologous functions of two amino acids with different chemical formula.

In the present context, the amino-terminal part of a polypeptide is understood as that part of the polypeptide in question or a portion thereof, measured in number of amino acids, which possesses a free α -$NH_2$ group at its end. The carboxy-terminal part of a polypeptide is understood as that part of the polypeptide in question or a portion thereof, measured in number of amino acids, which possesses a free α-COOH group at its end.

In one aspect of the invention, a signal peptide enabling the transport out of the cell may be linked to the amino-terminal end of the thermostable (1,3-1,4)-β-glucanase. The signal peptide may be one encoded by the relevant part of native (1,3-1,4)-β-glucanase genes in bacteria or other microorganisms such as yeast and fungi; it may be of synthetic origin, or a combination of these sources. The choice of signal peptide depends on the microorganism used for expression of the thermostable (1,3-1,4)-β-glucanase. Preferably, the signal peptide is a signal peptide homologous to the microorganism in question; e.g. when a yeast is used for expression the signal peptide should be homologous to yeast in order to enable transport of the thermostable (1,3-1,4)-β-glucanase out of the yeast cell. A suitable yeast signal peptide is the signal peptide from invertase which is known to be one of the few secreted proteins in yeast such as Saccharomyces species. However, also other signal peptides from yeast such as the signal peptide for α-factor and acid phosphatase may be used for transporting the thermostable (1,3-1,4)-β-glucanase out of the yeast cell.

In a preferred embodiment of the present invention the signal peptide is at least 75%, preferably at least 85%, more preferably at least 90% identical to the signal peptide of *Bacillus amyloliquefaciens* at the amino acid level as defined above.

In a still further aspect the invention relates to a thermostable (1,3-1,4)-β-glucanase which comprises the following amino acid sequence: (amino Acid residues 26–239 of SEQ ID NO: 2)

The invention also relates to a thermostable (1,3-1,4)-β-glucanase with the following amino acid sequence: (SEQ ID NO: 2)

Gln—Thr—Gly—Gly—Ser—Phe—Phe—Glu—Pro—Phe—Asn—Ser—Tyr—Asn—Ser—Gly—Leu—

Trp—Gln—Lys—Ala—Asp—Gly—Tyr—Ser—Asn—Gly—Asp—Met—Phe—Asn—Cys—Thr—Trp—

Arg—Ala—Asn—Asn—Val—Ser—Met—Thr—Ser—Leu—Gly—Glu—Met—Arg—Leu—Ala—Leu—

Thr—Ser—Pro—Ser—Tyr—Asn—Lys—Phe—Asp—Cys—Gly—Glu—Ans—Arg—Ser—Val—Gln—

Thr—Tyr—Gly—Tyr—Gly—Leu—Tyr—Glu—Val—Arg—Met—Lys—Pro—Ala—Lys—Asn—Thr—

Gly—Ile—Val—Ser—Ser—Phe—Phe—Thr—Tyr—Thr—Gly—Pro—Thr—Glu—Gly—Thr—Pro—

Trp—Asp—Glu—Ile—Asp—Ile—Glu—Phe—Leu—Gly—Lys—Asp—Thr—Thr—Lys—Val—Gln—

Phe—Asn—Tyr—Tyr—Thr—Asn—Gly—Val—Gly—Gly—His—Glu—Lys—Val—Ile—Ser—Leu—

Gly—Phe—Asp—Ala—Ser—Lys—Gly—Phe—His—Thr—Tyr—Ala—Phe—Asp—Trp—Gln—Pro—

Gly—Tyr—Ile—Lys—Trp—Tyr—Val—Asp—Gly—Val—Leu—Lys—His—Thr—Ala—Thr—Ala—

Asn—Ile—Pro—Ser—Thr—Pro—Gly—Lys—Ile—Met—Met—Asn—Leu—Trp—Asn—Gly—Thr—

Gly—Val—Asp—Asp—Trp—Leu—Gly—Ser—Tyr—Asn—Gly—Ala—Asn—Pro—Leu—Tyr—Ala—

Glu—Tyr—Asp—Trp—Val—Lys—Tyr—Thr—Ser—Asn or analogues thereof.

Met—Lys—Arg—Val—Leu—Leu—Ile—Leu—Val—Thr—Gly—Leu—Phe—Met—Ser—Leu—Cys—

Gly—Ile—Thr—Ser—Ser—Val—Ser—Ala—Gln—Thr—Gly—Gly—Ser—Phe—Phe—Glu—Pro—

Phe—Asn—Ser—Tyr—Asn—Ser—Gly—Leu—Trp—Gln—Lys—Ala—Asp—Gly—Tyr—Ser—Asn—

Gly—Asp—Met—Phe—Asn—Cys—Thr—Trp—Arg—Ala—Asn—Asn—Val—Ser—Met—Thr—Ser—

-continued

Leu—Gly—Glu—Met—Arg—Leu—Ala—Leu—Thr—Ser—Pro—Ser—Tyr—Asn—Lys—Phe—Asp—

Cys—Gly—Glu—Asn—Arg—Ser—Val—Gln—Thr—Tyr—Gly—Tyr—Gly—Leu—Tyr—Glu—Val—

Arg—Met—Lys—Pro—Ala—Lys—Asn—Thr—Gly—Ile—Val—Ser—Ser—Phe—Phe—Thr—Tyr—

Thr—Gly—Pro—Thr—Glu—Gly—Thr—Pro—Trp—Asp—Glu—Ile—Asp—Ile—Glu—Phe—Leu—

Gly—Lys—Asp—Thr—Thr—Lys—Val—Gln—Phe—Asn—Tyr—Tyr—Thr—Asn—Gly—Val—Gly—

Gly—His—Glu—Lys—Val—Ile—Ser—Leu—Gly—Phe—Asp—Ala—Ser—Lys—Gly—Phe—His—

Thr—Tyr—Ala—Phe—Asp—Trp—Gln—Pro—Gly—Tyr—Ile—Lys—Trp—Tyr—Val—Asp—Gly—

Val—Leu—Lys—His—Thr—Ala—Thr—Ala—Asn—Ile—Pro—Ser—Thr—Pro—Gly—Lys—Ile—

Met—Met—Asn—Leu—Trp—Asn—Gly—Thr—Gly—Val—Asp—Asp—Trp—Leu—Gly—Ser—Tyr—

Asn—Gly—Ala—Asn—Pro—Leu—Tyr—Ala—Glu—Tyr—Asp—Trp—Val—Lys—Tyr—Thr—Ser—

Asn or analogues thereof.

The generally accepted abbreviation codes for amino acids are given in the following table:

| Amino acid | Abbreviation |
|---|---|
| Alanine | Ala |
| Arginine | Arg |
| Asparagine | Asn |
| Aspartic acid | Asp |
| Asparagine or aspartic acid | Asx |
| Cysteine | Cys |
| Glutamine | Gln |
| Glutamic acid | Glu |
| Glutamine or glutamic acid | Glx |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophane | Trp |
| Tyrosine | Tyr |
| Valine | Val |

The term "analogue" is used in the present context to indicate an enzyme of a similar amino acid composition or sequence as the characteristic amino acid sequence derived from the (1,3-1,4)-β-glucanase of the invention, allowing for minor variations which do not have an adverse effect on the enzymatic activity and the thermostability of the analogue. The analogous polypeptide or protein may be derived from other microorganisms than B. amyloliquefaciens and B. macerans or may be partially or completely of synthetic origin.

The amino acids of the (1,3-1,4)-β-glucanase may optionally have been modified, e.g. by chemical, enzymatic or another type of treatment, which does not effect adversely the specific activity of the (1,3- 1,4)-β-glucanase and its thermostability to any substantial extent.

In a further aspect, the invention relates to a DNA fragment comprising a nucleotide sequence encoding the thermostable hybrid (1,3 -1,4)-β-glucanase as described above. The DNA fragment may be used in a method of preparing the (1,3-1,4)-β-glucanase by recombinant DNA techniques. The use of the DNA fragment of the invention in the production of a recombinant (1,3-1,4)-β-glucanase (e.g. by inserting the fragment in a suitable vector, transforming a suitable host microorganism with the vector, cultivating the microorganism so as to produce the (1,3-1,4)-β-glucanase and subsequently recovering the enzyme from the microorganisms) includes a number of advantages. It is thus possible to provide large amounts of the (1,3-1,4)-β-glucanase and the enzyme produced may be isolated in a substantially pure form, free from contaminating substances.

The (1,3-1,4)-β-glucanase of the invention may also be prepared by the well-known methods of liquid or solid phase peptide synthesis utilizing the successive coupling of the individual amino acids of the polypeptide sequence or the coupling of individual amino acids forming fragments of the polypeptide sequence which are subsequently coupled so as to result in the desired polypeptide. The solid phase peptide synthesis may e.g. be performed as described by Merrifield (1963). In solid phase synthesis, the amino acid sequence is constructed by coupling an initial amino acid to a solid support and then sequentially adding the other amino acids in the sequence by peptide bonding until the desired length has been obtained. The preparation of synthetic peptides for use for diagnostic purposes may be carried out essentially as described in Shinnick (1983).

In a particular aspect, the present invention relates to a DNA fragment substantially comprising the nucleotide sequence: (SEQ ID NO: 1)

```
                    30                            60
GAATTCAACG AAGAATCGCT GCACTATTAT CGATTCGTCA CCCACTTAAA GTTTTTCGAC
                    90                           120
CAGCGTCTTT TTAACGGCAC ACACATGGAA AGCCAGGACG ATTTTTTACT GGAGACAGTG
```

-continued

```
                150                                              180
AAAGAAAAGT ATCATCAGGC GTATAAATGC ACGAAGAATA TCCATACCTA CATTGAGAAA 210                                              240
GAGTATGGGC ATAAGCTCAC CAGTGACGAG CTGCTGTATT TAACGATTCA CATAGAAAGG 270                                              300
GTAGTCAAAC AAGTATAATG AAAGCGCTTT CCTCGTATTA ATTGTTTCTT CCATTCATAT 330                                              360
ATAGGATTGT TACGGATAAA GCAGGCAAAA CCTATCTGTC TGTGCTGATG GTAGTTTAGG 390                                              420
TTTGTATTTT TAACAGAAGG ATTATCATTA TTTCGACCGA TGTTCCCTTT GAAAAGGATC 450                                              480
ATGTATGATC AATAAAGAAA GCGTGTTCAA AAAAGGGGGA ATGCTAACAT GAAACGAGTG 510                                              540
TTGCTAATTC TTGTCACCGG ATTGTTTATG AGTTTGTGTG GGATCACTTC TAGTGTTTCG 570                                              600
GCTCAAACAG GCGGATCGTT TTTTGAACCT TTTAACAGCT ATAACTCCGG GTTATGGCAA 630                                              660
AAAGCTGATG GTTACTCAAA TGGAGATATG TTTAACTGCA CTTGGCGTGC TAATAACGTC 690                                              720
TCTATGACGT CATTAGGTGA AATGCGTTTG GCGCTGACAA GTCCGTCTTA TAACAAGTTT 750                                              780
GACTGCGGGG AAAACCGCTC GGTTCAAACA TATGGCTATG GACTTTATGA AGTCAGAATG 810                                              840
AAACCGGCTA AAAACACAGG GATTGTTTCA TCGTTCTTCA CTTATACAGG TCCAACGGAG 870                                              900
GGGACTCCTT GGGATGAGAT TGATATCGAA TTTCTAGGAA AAGACACGAC AAAAGTGCAG 930                                              960
TTTAACTATT ATACCAATGG GGTTGGCGGT CATGAAAAGG TTATCTCTCT TGGCTTTGAT 990                                             1020
GCATCAAAGG GCTTCCATAC CTATGCTTTC GATTGGCAGC CAGGGTATAT TAAATGGTAT 1050                                             1080
GTAGACGGTG TTTTGAAACA TACCGCCACC GCGAATATTC CGAGTACGCC AGGCAAAATT 1110                                             1140
ATGATGAATC TATGGAACGG AACCGGAGTG GATGACTGGT TAGGTTCTTA TAATGGAGCG 1170                                             1200
AATCCGTTGT ACGCTGAATA TGACTGGGTA AAATATACGA GCAATTAATA TGATTGCAGC

1230
TGGGCATGAG CTTTTTAGTC CACTCCAGGC ATGCAAGCTT
``` or an analogue or a subsequence thereof.

Each of the nucleotides of the above sequence is represented by the abbreviations generally used, i.e.

A represents adenine

T represents thymidine

G represents guanine

C represents cytosine

In the present context, the term "analogue" is intended to designate a DNA fragment which shows one or several modifications in the nucleotide sequence, the modifications being of such a character that the modified DNA fragment is capable of encoding a hybrid (1,3-1,4)-β-glucanase having temperature stability properties as defined above. The modifications include, e.g., base substitutions which do not affect the resulting amino acid sequence encoded by the DNA fragment, substitutions of single base pairs resulting in the encoding of functionally equivalent amino acids, deletions, and additions. In the present context, the term "subsequence" designates a DNA sequence which comprises part of the DNA sequence shown above or other DNA sequences of the invention and which has retained its capability of expressing a (1,3-1,4)-β-glucanase having temperature stability properties as defined above, including subsequences which have been analogized by modifications as explained above.

The DNA fragment encoding the (1,3-1,4)-β-glucanase or a part thereof may be subjected to mutagenization, e.g. by treatment with ultraviolet radiation, ionizing radiation or a chemical mutagen such as mitomycin C, 5-bromouracil, methylmethane sulphonate, hydroxylamine, nitrogen mustard or a nitrofuran so as to alter some of the properties of the gene product expressed from the mutagenized sequence substantially without effecting the enzymatic activity and the thermostability properties of the gene product. Especially, site-directed mutagenesis or directed mutagenesis is useful in order to improve the thermostability, pH optimum for enzymatic activity and other useful properties of the (1,3-1,4)-β-glucanase.

The DNA fragment of the invention may be one which has been modified by substitution, addition, insertion or deletion of one or more nucleotides in the sequence for the purpose of establishing a sequence which, when expressed in a suitable host organism, results in the production of a (1,3-1,4)-β-glucanase having the temperature stability properties as defined above.

Also, in a still further aspect, the present invention relates to a method for producing a thermostable (1,3-1,4)-β-glucanase comprising cultivating a microorganism in which a DNA fragment as described above has been introduced in such a way that the microorganism is capable of producing the thermostable (1,3-1,4)-β-glucanase, the cultivation being performed under conditions leading to production of the thermostable (1,3-1,4)-β-glucanase and recovering the (1,3-1,4)-β -glucanase from the culture.

Suitable expression vectors for the production of (1,3-1,4)-β-glucanase or a part thereof are vectors which upon transformation of a host organism are capable of replicating in the host organism. The vector may either be one which is capable of autonomous replication, such as a plasmid, or one which is replicated with the host chromosome, such as a bacteriophage. Examples of suitable vectors which have been widely employed are pBR322 and related vectors as well as pUC vectors and the like. Examples of suitable bacteriophages include M13 and λ. Examples of self-replicating yeast vectors are those vectors carrying that part of the yeast 2μ DNA which is responsible for autonomous replication.

The organism harbouring the vector carrying the DNA fragment of the invention or part thereof may be any organism which is capable of expressing said DNA fragment. The organism is preferably a microorganism such as a yeast or a bacterium. Yeasts such as Saccharomyces species possess some inherent properties which may be of great advantage in the production of extracellular proteins. Normally, yeasts only secrete very few proteins to the medium wherein they are cultured. It is, therefore, relatively easy to isolate and purify a yeast produced recombinant protein if this protein can be secreted from the yeast cell. In order to obtain secretion of the thermostable (1,3-1,4)-β-glucanase a signal peptide must be linked to the N-terminal end of the enzyme. The yeast-produced enzyme invertase is one of the few yeast proteins which are secreted from the yeast cell and it is therefore anticipated that the signal peptide from yeast invatase is suitable for enabling transport out of the yeast cell of the thermostable (1,3-1,4)-β-glucanase. However, gram-positive microorganisms as well as gram-negative bacteria may be employed as host organisms. Especially, a gram-negative bacterium such as E. coli is useful, but also gram-positive bacteria such as B. subtilis and other types of microorganisms such as fungi or other microorganisms conventionally used to produce recombinant DNA products may be used.

When a microorganism is used for expressing the DNA fragment of the invention, the cultivation conditions will typically depend on the type of microorganism employed, and a person skilled in the art will know which cultivation method to choose and how to optimize this method.

In a still further aspect the invention relates to a plant capable of expressing the DNA fragment as described above. It may be advantageous to construct a plant which is able to express in its grains and germlings a thermostable (1,3-1,4)-β-glucanase as this can eliminate the need for adding the enzyme to, e.g. the mash during the brewing process. Preferably, the plant is oat, barley, rye, wheat, rice or maize or any other plant used in the production of beer, coffee surrogates, feed or other manufacturing processes where the degradation of β-glucans by (1,3-1,4)-β-glucanases is required. A plant with an increased (1,3-1,4)-β-glucanase activity as compared to the plant in its natural form is, e.g. advantageous as a raw material for the production of beer because an increased β-glucanase activity will lead to a decreased amount of β-glucans in the wort which makes the filtration easier and improves the quality of the final product. Accordingly, the present invention relates to a genetic construct useful for producing a thermostable (1,3-1,4)-β-glucanase as defined above, i.e. a (1,3-1,4)-β-glucanase encoded by a DNA fragment as described above which construct comprises 1) a regulatory sequence functionally connected to 2) a DNA fragment as defined above encoding the (1,3-1,4)-β-glucanase, possibly including a nucleotide sequence encoding a signal peptide and 3) a transcription termination DNA sequence, functionally connected to the DNA fragment of 2).

The genetic construct useful for producing a (1,3-1,4)-β-glucanase of the invention, or a part thereof, is preferably used in the construction of a plant having an increased β-glucanase activity as compared to a plant not containing the genetic construct. However, this need not be the case since a plant expressing the DNA fragment of the invention may have a lower β-glucanase activity but a β-glucanase activity which is retained at high temperatures. When constructing a plant producing a temperature tolerant β-glucanase and possibly having an increased β-glucanase activity relative to the non-modified plant, the genetic construct should be active in a tissue or cell in which the (1,3-1,4)-β-glucanase is required for the desired activity or from which the β-glucanase may be transported into the place of activity. The genetic construct may be inserted in connection with or instead of another (1,3-1,4)-β-glucanase gene and may be inserted under the control of the regulatory sequence of a plant gene so that no additional regulatory sequence is required. However, in certain plants such as maize, rice and wheat no (1,3-1,4)-β-glucanase gene is present and it will therefore, in order to obtain expression of the inserted β-glucanase gene in the plant, be necessary to introduce regulatory sequences to control the expression of the inserted β -glucanase gene or, alternatively, employ other regulatory sequences in the plant to control expression. The introduction of DNA into a plant cell may e.g. be carried out by direct injection of DNA into naked protoplasts or by firing DNA-coated particles into the cell or protoplast.

The regulatory sequence contained in the above defined genetic constructs is preferably a plant promoter such as a constitutive or regulatable plant promoter. When the genetic construct is to be used in a genetically modified plant, the promoter is preferably a promoter active in a plant which may be the CaMV promoter, the NOS promoter or the (1,3-1,4)-β-glucanase promoter. The examples of promoters are illustrative, other sequences can fulfill the same need. The transcription termination sequence of the genetic construct is a nucleotide sequence capable of terminating the transcription of a DNA fragment of gene and providing a polyadenylation signal and is preferably derived from a plant, i.e. being a plant transcription termination sequence.

The genetic construct may further be provided with a marker which allows for the selection of the genetic construct in a plant cell into which it has been transferred.

Various markers exist which may be used in plant cells, particularly markers which provide for antibiotic resistance. These markers include resistance to G418, hygromycin, bleomycin, kanamycin and gentamycin.

In recent years, considerable effort has been focused on developing useful methods for constructing novel plants or plant cells having specific and desirable properties, and a number of such methods based on recombinant DNA technology and suitable plant transformation systems are now available. It is contemplated that plants of the invention, e.g. plants having the properties described above, may be constructed by use of such methods.

The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a bacterial vector system. Thus, in another aspect, the present invention relates to introducing a gene plus a genetic construct as defined above into the genome of a plant such as oat, barley, rye, wheat, rice or maize.

When plant cells with new genetic information are constructed, these cells may be grown and maintained in accordance with well-known tissue culturing methods such as culturing the cells in a suitable culture medium supplied with the necessary growth factors such as amino acids, plant hormones, vitamins etc.

As mentioned previously, it is especially advantageous to use the thermostable (1,3-1,4)-β-glucanase of the invention in the production of beer. During the mashing process, β-glucans are extracted from the malt leading to an increased viscosity of the mash. In order to reduce the amount of β-glucans in the mash and the wort, the thermostable (1,3-1,4)-β-glucanase should be added during the mashing process. In some breweries, the mashing process is carried out as a stepwise process where the temperature is gradually raised up to a maximum temperature as high as about 76° C. In other breweries, the mashing process is carried out at a fixed temperature, typically in an interval from 50° to 65° C. The (1,3-1,4)-β-glucanase present in the barley becomes inactivated at about 55° C. and commercially available products such as Cereflo® (a composite enzyme product comprising a (1,3-1,4)-β-glucanase available from Novo-Nordisk A/S, Denmark) becomes inactivated at about 67° C. Due to the high thermostability and high specific activity of the (1,3-1,4)-β-glucanase of the present invention, addition of a much lower amount of this enzyme is sufficient to achieve degradation of the β-glucans in the mash. While it is necessary to add 4 mg of Cereflo® pr. kg of malt in order to degrade the β-glucans present in a typical mash, it is anticipated that a much lower amount of the thermostable (1,3-1,4)-β-glucanase of the present invention is sufficient to achieve the same result. An amount of the thermostable (1,3-1,4)-β-glucanase as low as 20 µg/kg malt or even lower is believed to be sufficient to degrade the β -glucans in a typical mash.

Thus, the invention further relates to a method of degrading (1,3 -1,4)-β-glucans in a substrate, which method comprises subjecting the substrate to the action of an effective amount of a thermostable (1,3-1,4)-β-glucanase as described above for an appropriate period of time at a temperature of 65° C. or higher, the amount of (1,3-1,4)-β-glucanase being at the most 200 µg, preferably at the most 100 µg, more preferably at the most 50 µg, still more preferably at the most 20 µg, and most preferably at the most 15 µg pr. kg of substrate.

The β-glucan containing substrate may be in solid or liquid form and may comprise different types of raw grains such as oat or barley, or parts and mixtures thereof. The (1,3-1,4)-β-glucanase enzyme may be added in purified form, or as part of a mixture containing other enzymes or subsidiary materials, the enzyme preferably being solubilized. Also, the enzyme may be contained in the substrate by being incorporated in the plant by genetic engineering.

The substrate comprising (1,3-1,4)-β-glucans may also be mixed with a second substrate containing a thermostable (1,3-1,4)-β-glucanase, the second substrate originating from maize, rice or wheat. Maize, rice and wheat does not naturally produce (1,3-1,4)-β-glucanase but can be changed by genetic engineering techniques to incorporate and express a gene encoding a thermostable (1,3-1,4)-β-glucanase.

The invention will now be further described with reference to the accompanying drawings and the following Examples.

LEGEND TO FIGURES

FIG. 1. Construction of an *E. coli* expression and secretion vector containing the hybrid gene bgl-H1. bgl-A: (1,3-1,4)-β-glucanase gene from *B. amyloliquefaciens*. bgl-M: (1,3-1,4)-β-glucanase gene from *B. macerans*. For details, see Example 1.

Figure 2:
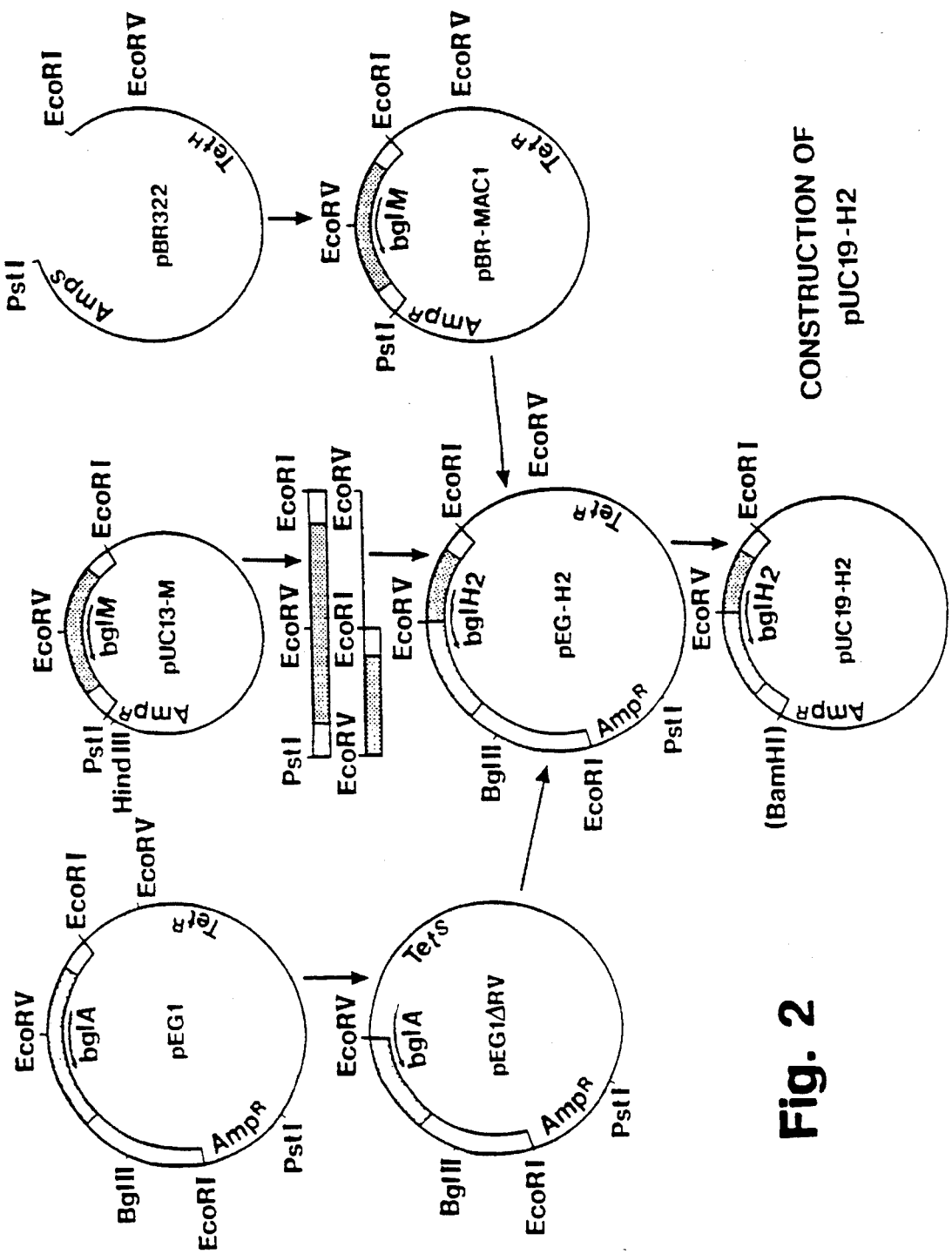

FIG. 2. Construction of an *E. coli* expression and secretion vector containing the hybrid gene bgl-H2. bgl-A: (1,3-1,4)-β-glucanase gene from *B. amyloliquefaciens*. bgl-M: (1,3-1,4)-β-glucanase gene from *B. macerans*. For details, see Example 1.

Figure 3:
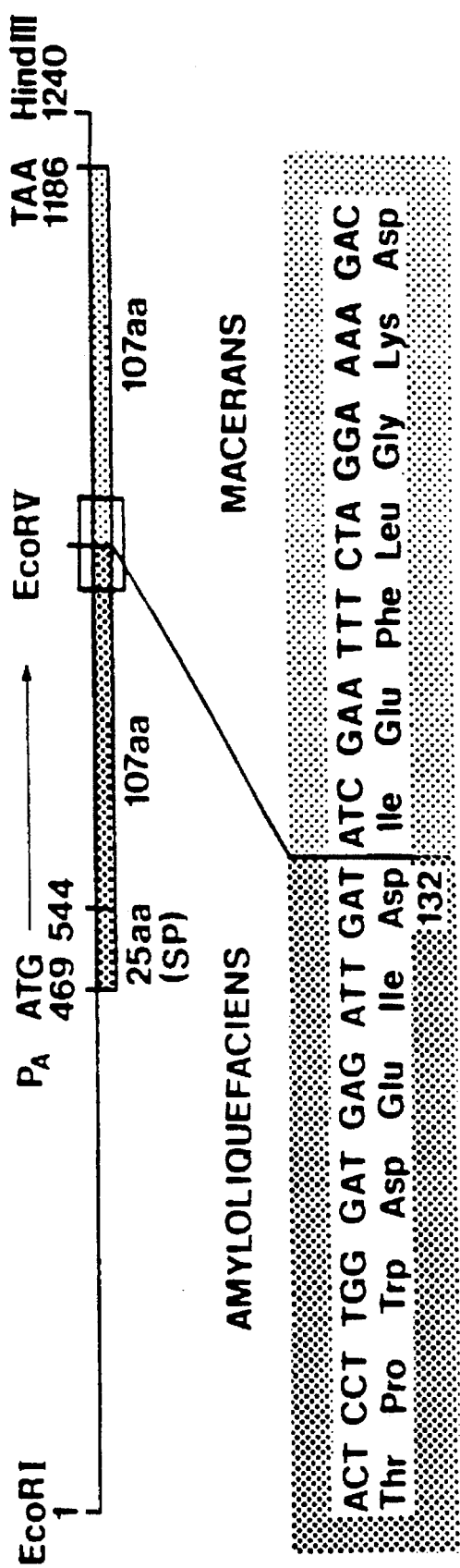

FIG. 3. Diagram of the bgl-H1 gene and details of the fusion region. SP: signal peptide. (The full sequence is shown in SEQ ID NO: 1)

Figure 4:
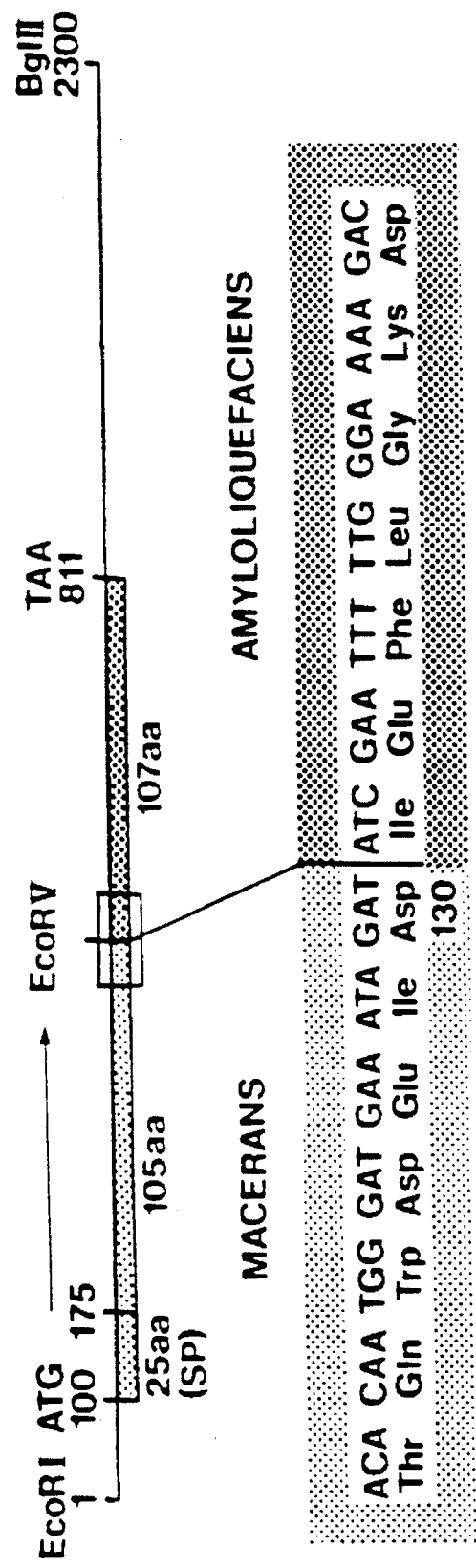

FIG. 4. Diagram of the bgl-H2 gene and details of the fusion region. SP: signal peptide. (The full sequence is shown in SEQ ID NO: 3)

Figure 5:
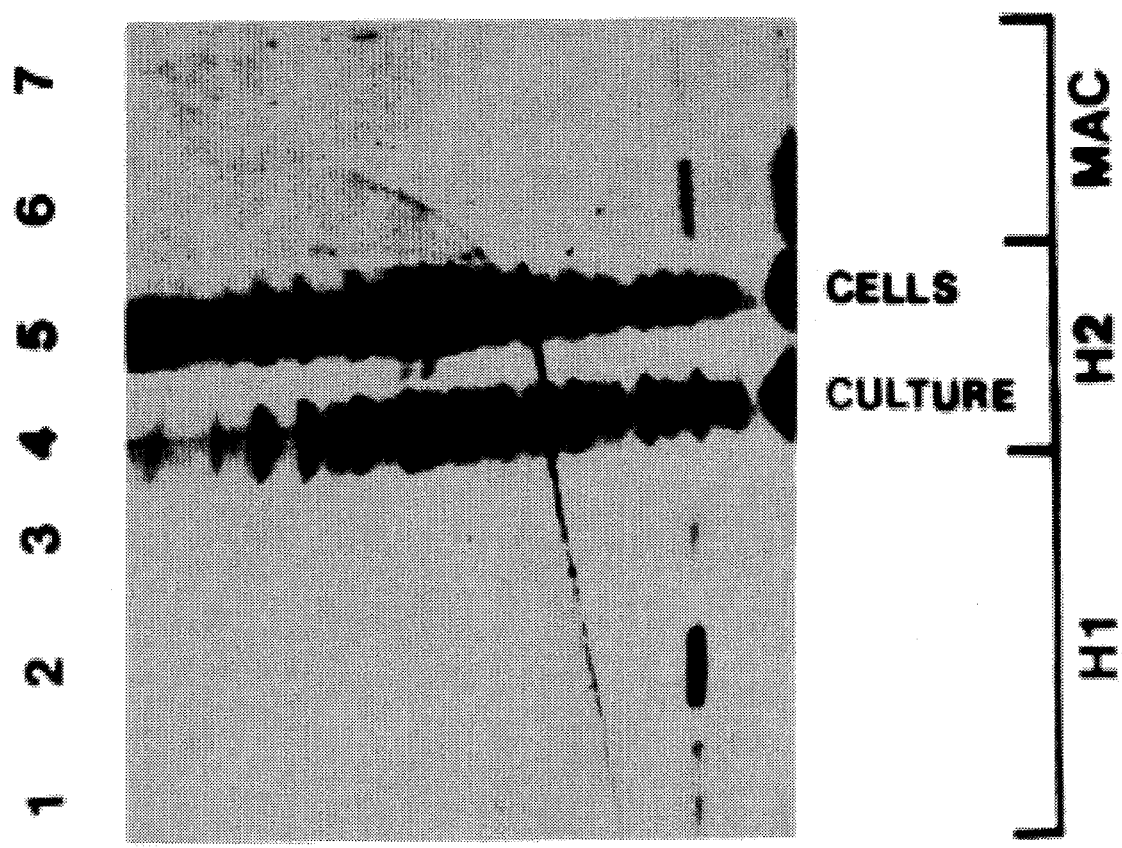

FIG. 5. SDS-PAGE of samples containing hybrid β-glucanases and *B. macerans* β-glucanase. Lanes 1–3: 2 µg, 5 µg, and 1 µg purified β -glucanase H1. Lanes 4: sample containing 50 µg supernatant protein and lane 5: 100 µg cell extract of *E. coli* cells transformed by pUC-H2. Lane 6: 2 µg of partially purified *B. macerans* β-glucanase. Lane 7: 1 µg of purified *B. macerans* β-glucanase.

Figure 6:
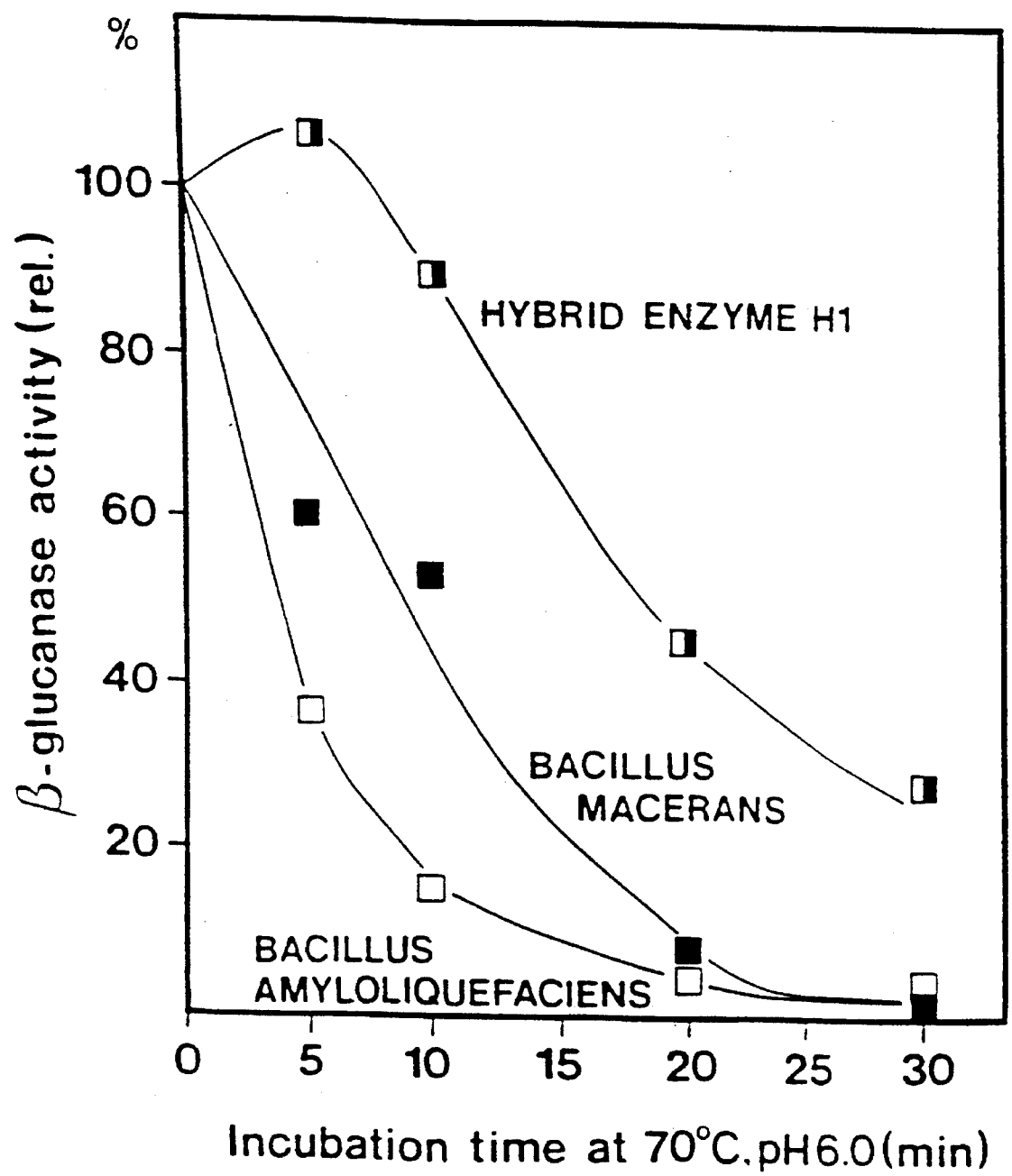

FIG. 6. Activity of Bacillus hybrid β-glucanase H1 and parental enzymes in crude extracts from transgenic *E. coli* cells after incubation for various lengths of time at 70° C., pH 6.0. Activity is expressed as per cent of the activity at time 0.

Figure 7:
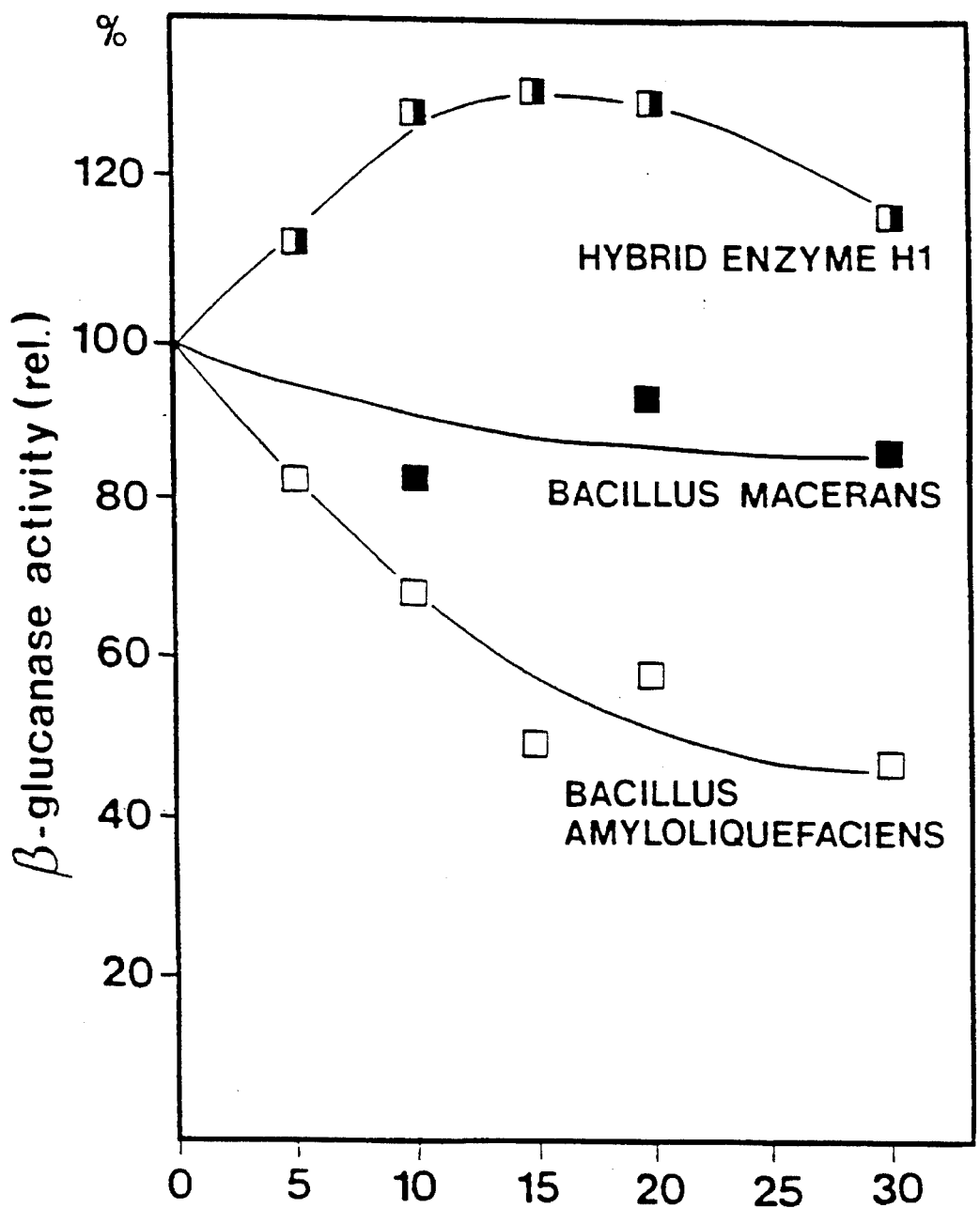

FIG. 7. Activity of hybrid Bacillus β-glucanase H1 and parental enzymes in crude extracts (see Materials and Methods) from transgenic *E. coli* cells after incubation for various lengths of time at 65° C., pH 6.0. Activity is expressed as per cent of the activity at time 0.

Figure 8:
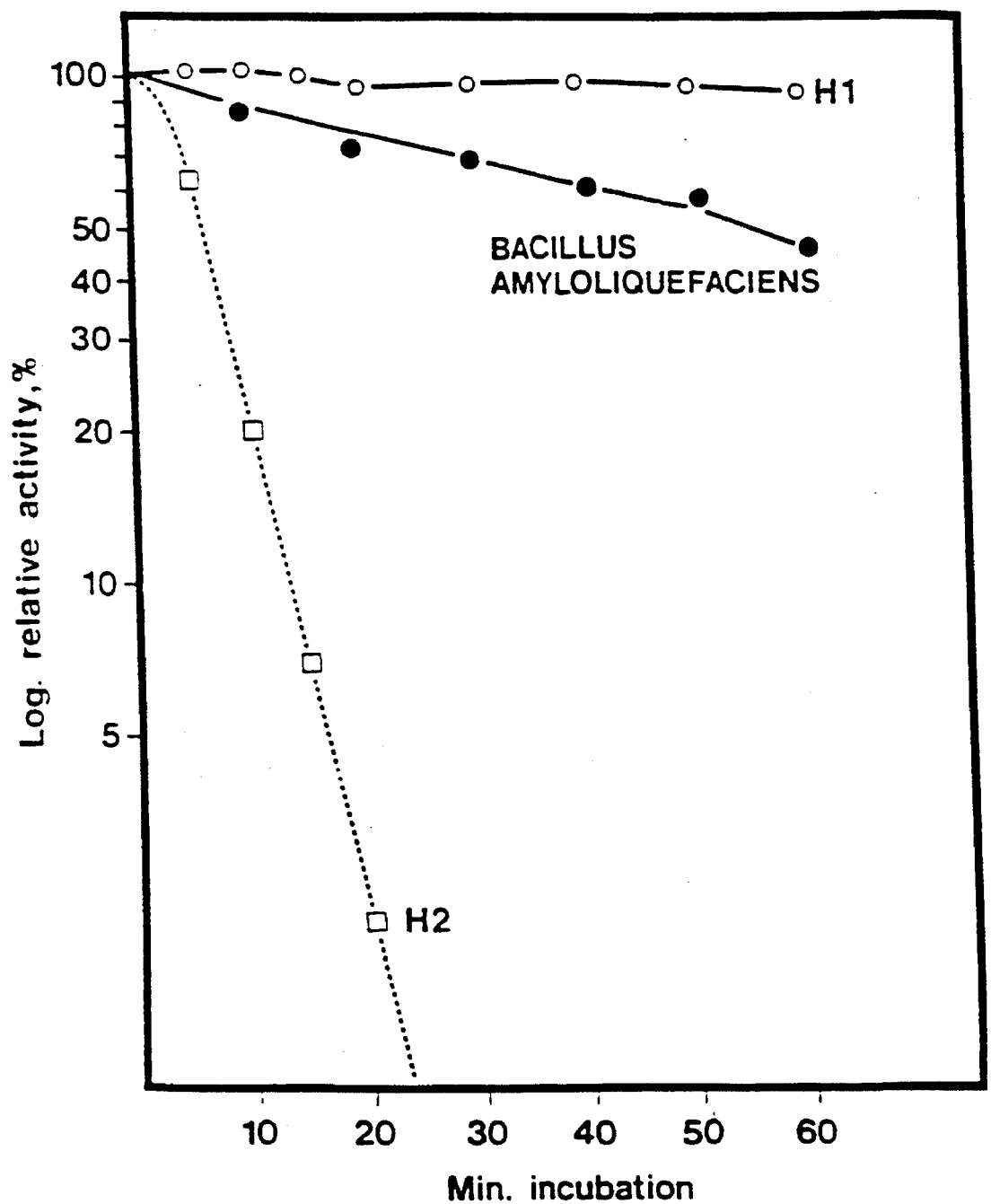

FIG. 8. Time course of thermoinactivation of Bacillus hybrid β -glucanases H1 and H2 at 65° C., pH 5.5 in comparison with the β-glucanase of *B. amyloliquefaciens*. The purified *amyloliquefaciens* and H1 -enzymes were dissolved at a concentration of 1 µg·ml$^{-1}$ in 40 mM Na-acetate, pH 5.5, 10 mM CaCl$_2$ and 50 µg·ml$^{-1}$ bovine serum albumin. The H2-enzyme preparation was dissolved at a protein concentration of 0.75 mg·ml$^{-1}$ in an identical buffer. Samples were withdrawn periodically and assayed for residual β-glucanase activity.

Figure 9:
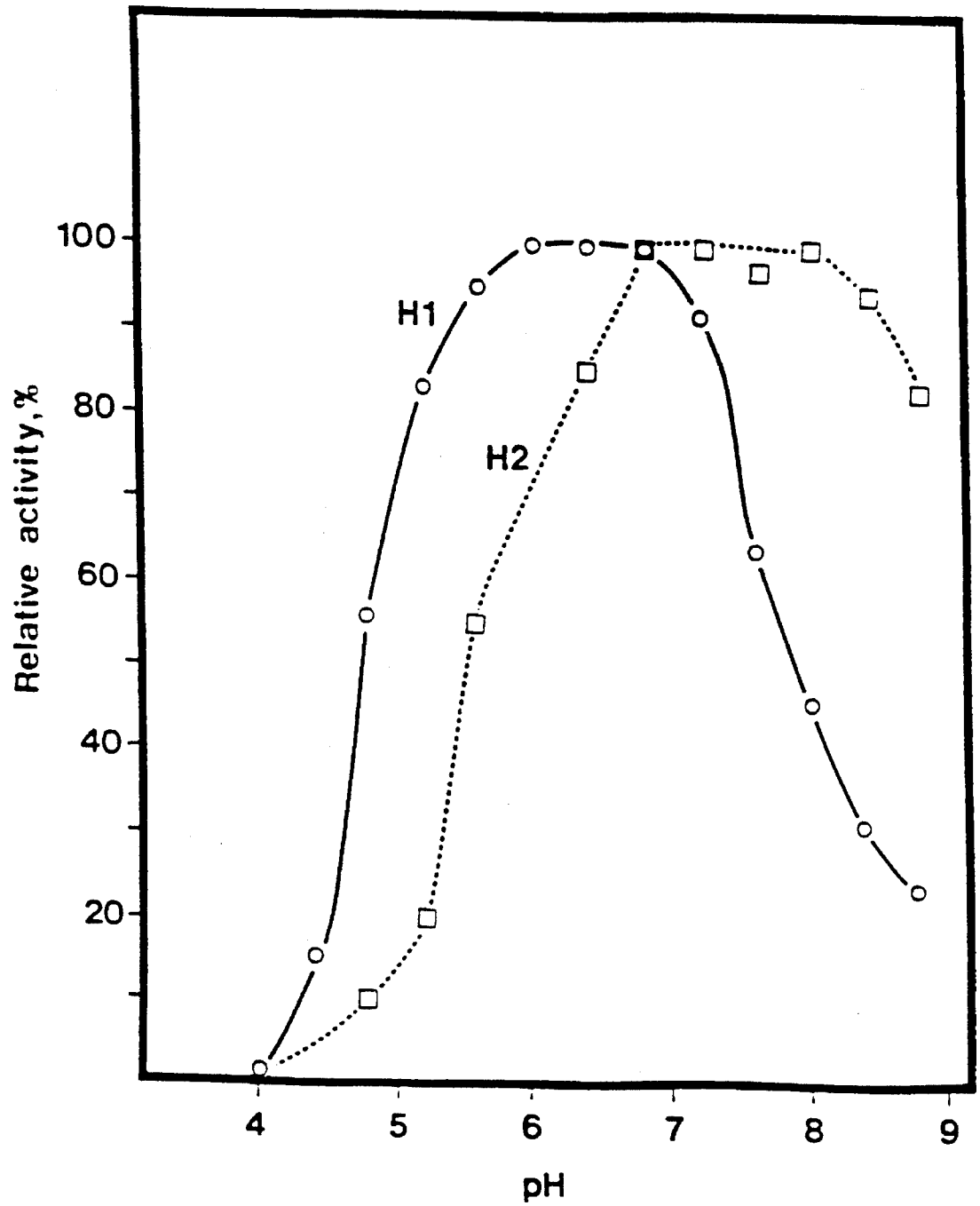

FIG. 9. The pH dependence of the activity of Bacillus hybrid β-glucanases H1 and H2. The reactions were carried out with 1–6 μg H1 β-glucanase and 7–70 μg H2 β-glucanase preparation in the following buffers: 40 mM Na-acetate, pH 3.6–5.6; 40 mM K/Na phosphate, pH 6–8 and 40 mM Tris-Hcl, pH 8.4–8.8. Activity was determined with the Biocon assay using azo-barley β-glucan as substrate (McCleary, 1988).

FIG. 10. Activity of Bacillus hybrid β-glucanase H1 and parental enzymes in crude extracts from transgenic E. coli cells after incubation for various lengths of time at 65° C., pH 4.0. Activity is expressed as per cent of the activity at time 0.

Figure 11:
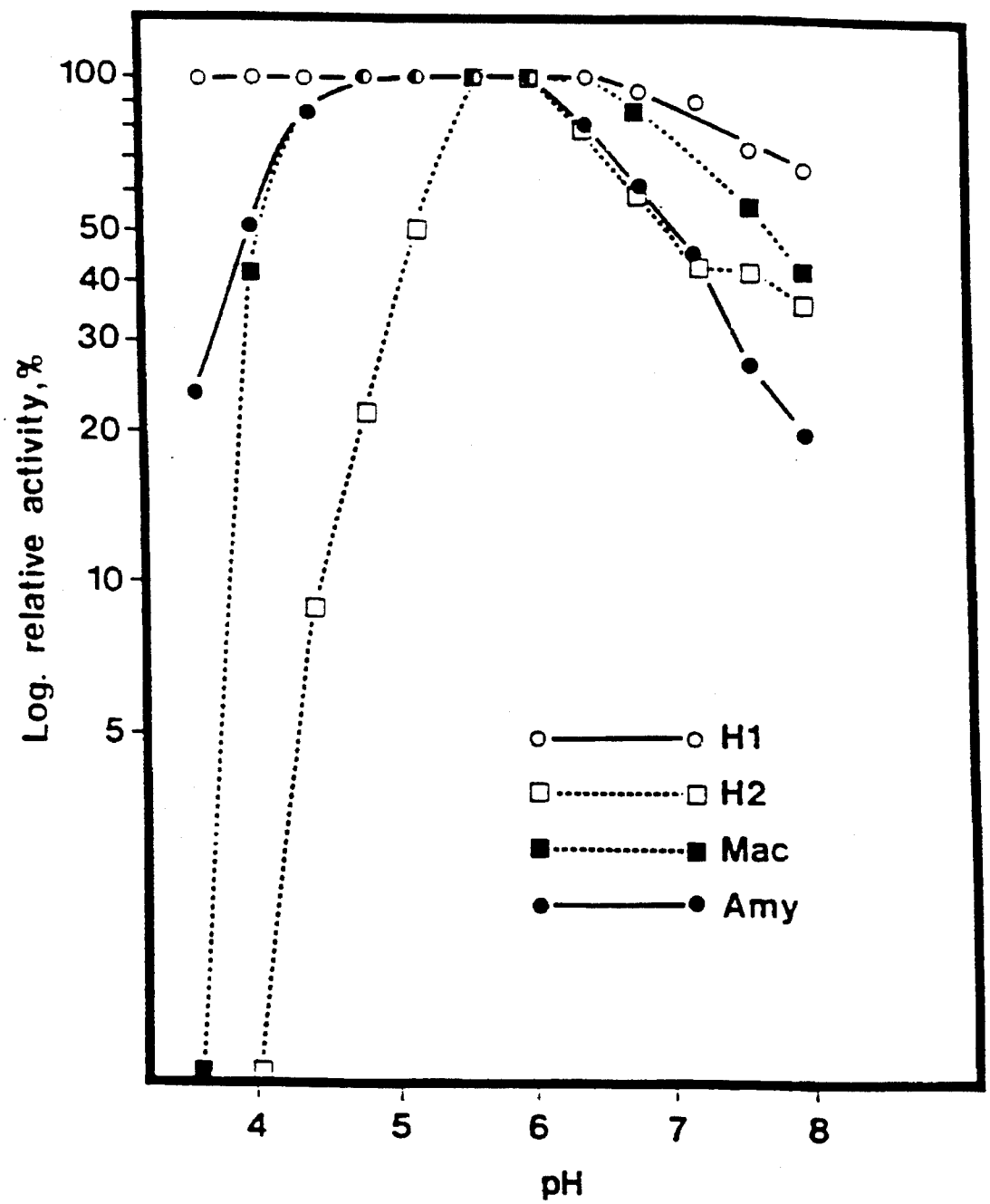

FIG. 11. The pH dependence of stability of Bacillus β-glucanase at 55° C. 2 μg of hybrid β-glucanase H1, 375 μg protein of hybrid β-glucanase H2 preparation, 2 μg of B. macerans β-glucanase (Mac) or 10 μg of B. amyloliquefaciens β-glucanase (Amy) were tested with 10 mM CaCl and 50 μg·ml$^{-1}$ bovine serum albumin in 40 mM Na-acetate buffer adjusted to the indicated pH values in the range of 3.6 to 5.6 or in 40 mM K/Na phosphate buffer adjusted to the indicated pH values in the range 6.0 to 8.0. After incubation for 1 h at 55° C. the residual activity was measured with method A (see Materials and Methods).

Figure 12:
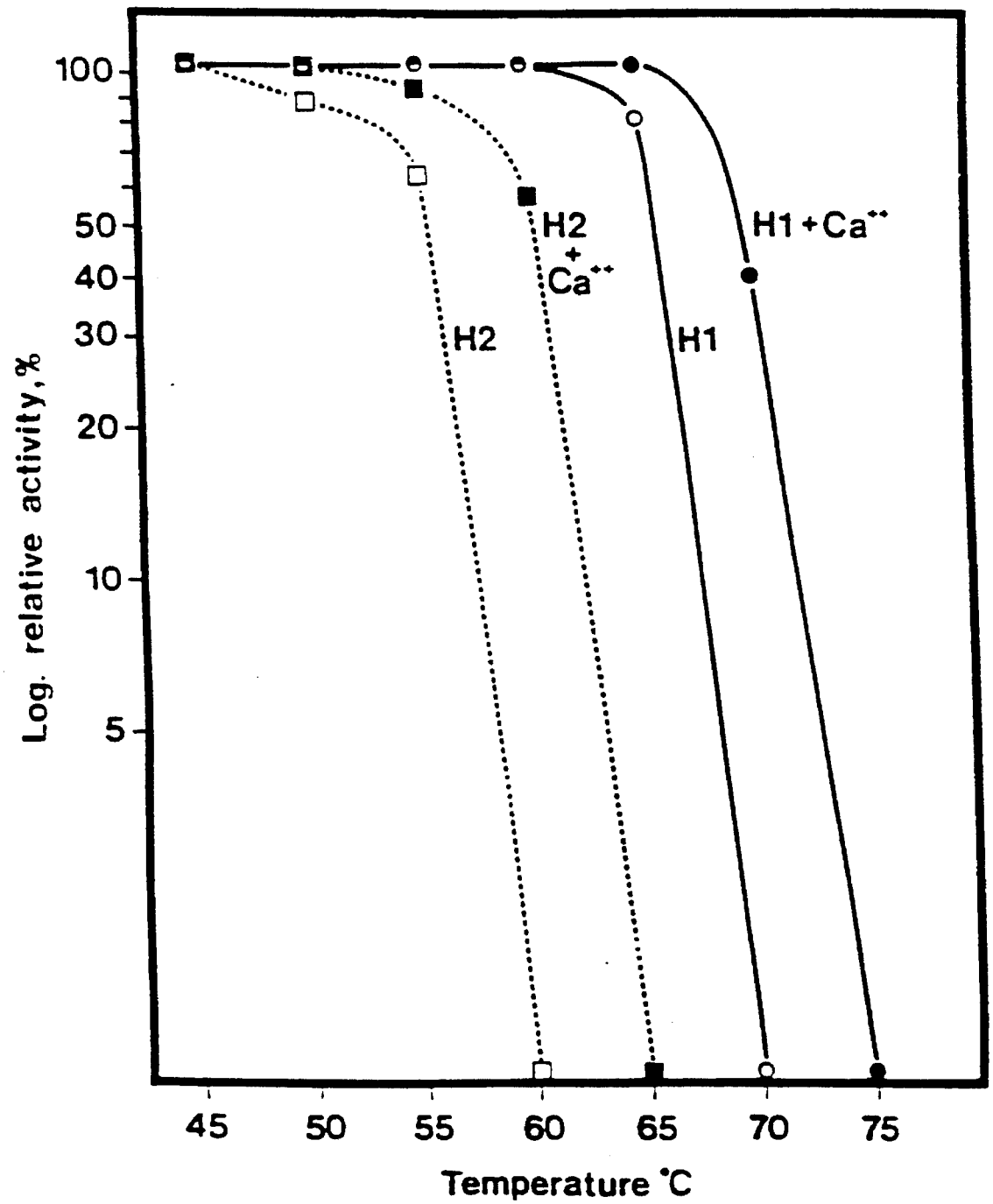

FIG. 12. Improvement of thermal stability of Bacillus hybrid β-glucanases in the presence of $CaCl_2$. 0.1 μg Bacillus hybrid enzyme H1 or 750 μg hybrid enzyme H2 preparation was dissolved in 1 ml 40 mM Na-acetate buffer pH 5.5 with or without 50 mM $CaCl_2$ and supplemented with 50 μg·ml$^{-1}$ bovine serum albumin. After incubation for 30 min. at the indicated temperatures the residual activity was determined.

Figure 13:
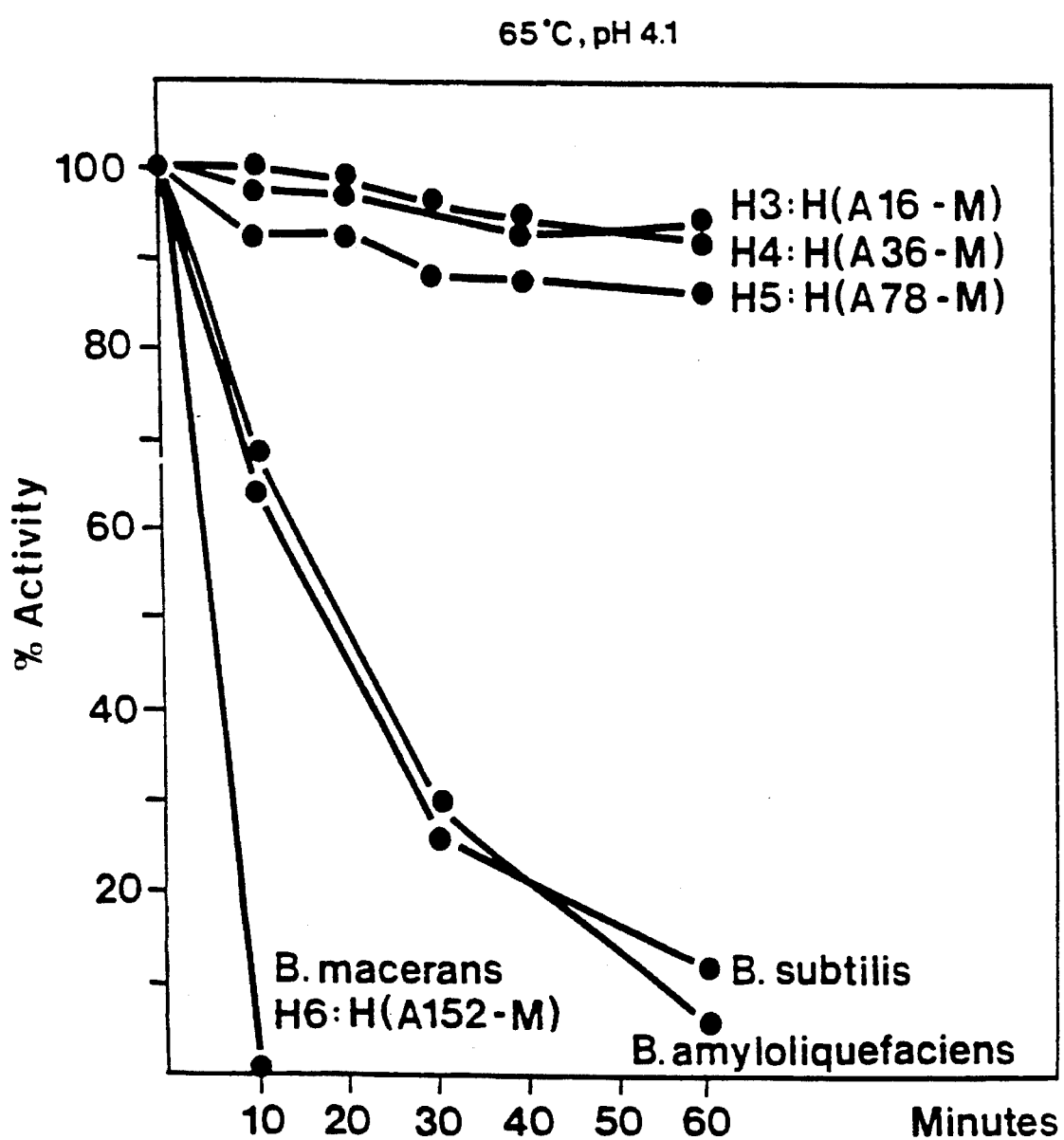

FIG. 13. Time course of thermoinactivation of purified Bacillus hybrid β-glucanases H3, H4, H5 and H6 at 65° C., pH 4.1 in comparison with purified native β-glucanases of B. amyloliquefaciens, B. macerans, and B. subtilis. The enzymes were dissolved at a concentration of 0.1 mg·ml$^{-1}$ in 40 mM Na-acetate buffer, pH 4.1, 10 mM $CaCl_2$. Samples were withdrawn periodically and assayed for residual β-glucanase activity.

Figure 14:
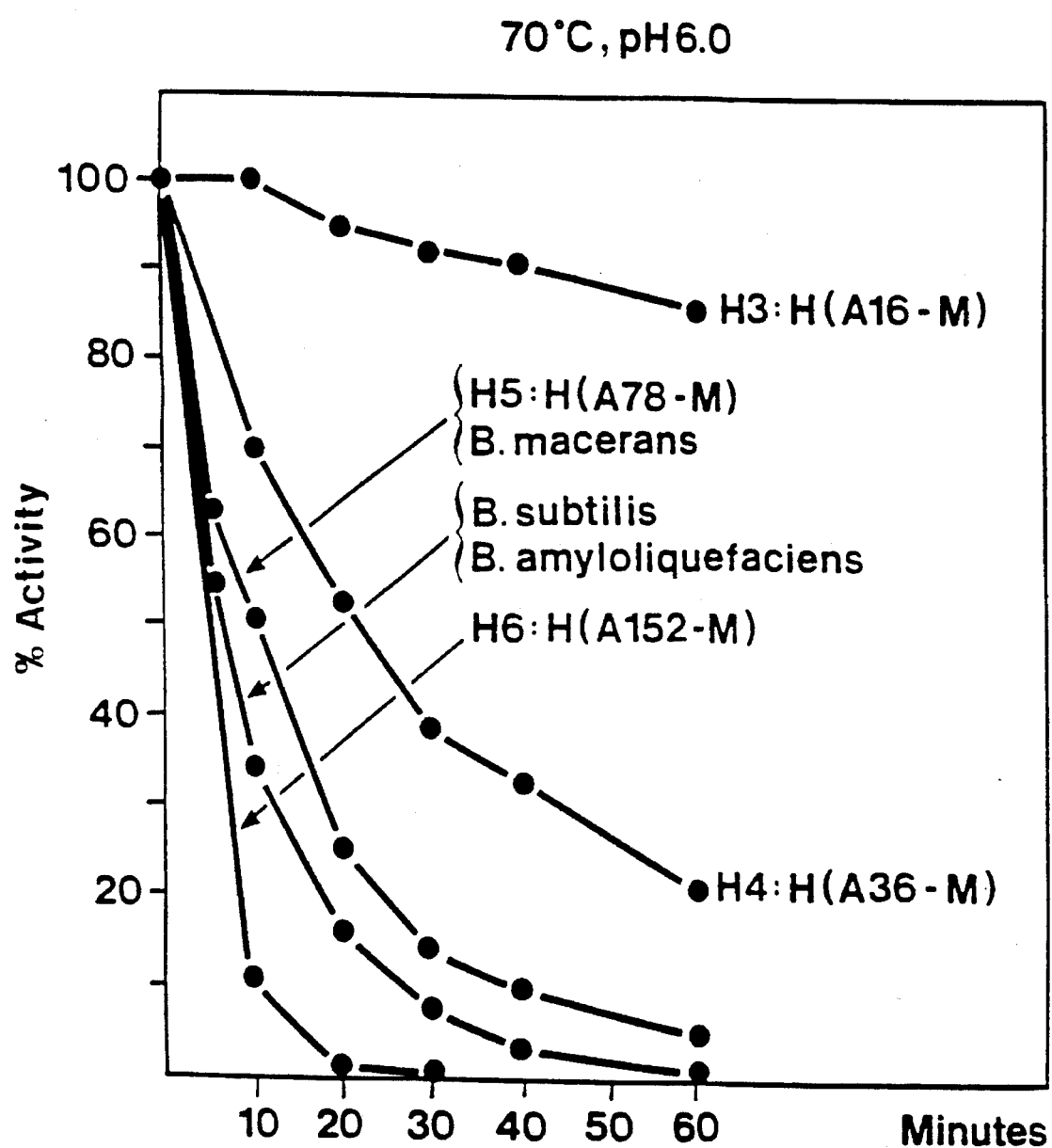

FIG. 14. Time course of thermoinactivation of purified Bacillus hybrid β-glucanases H3, H4, H5 and H6 at 70° C., pH 6.0 in comparison with purified native β-glucanases of B. amyloliquefaciens, B. macerans, and B. subtilis. The enzymes were dissolved at a concentration of 0.1 mg·ml$^{-1}$ in 40 mM Na-acetate buffer, pH 5.5, 10 mM $CaCl_2$. Samples were withdrawn periodically and assayed for residual β-glucanase activity.

Figure 15:
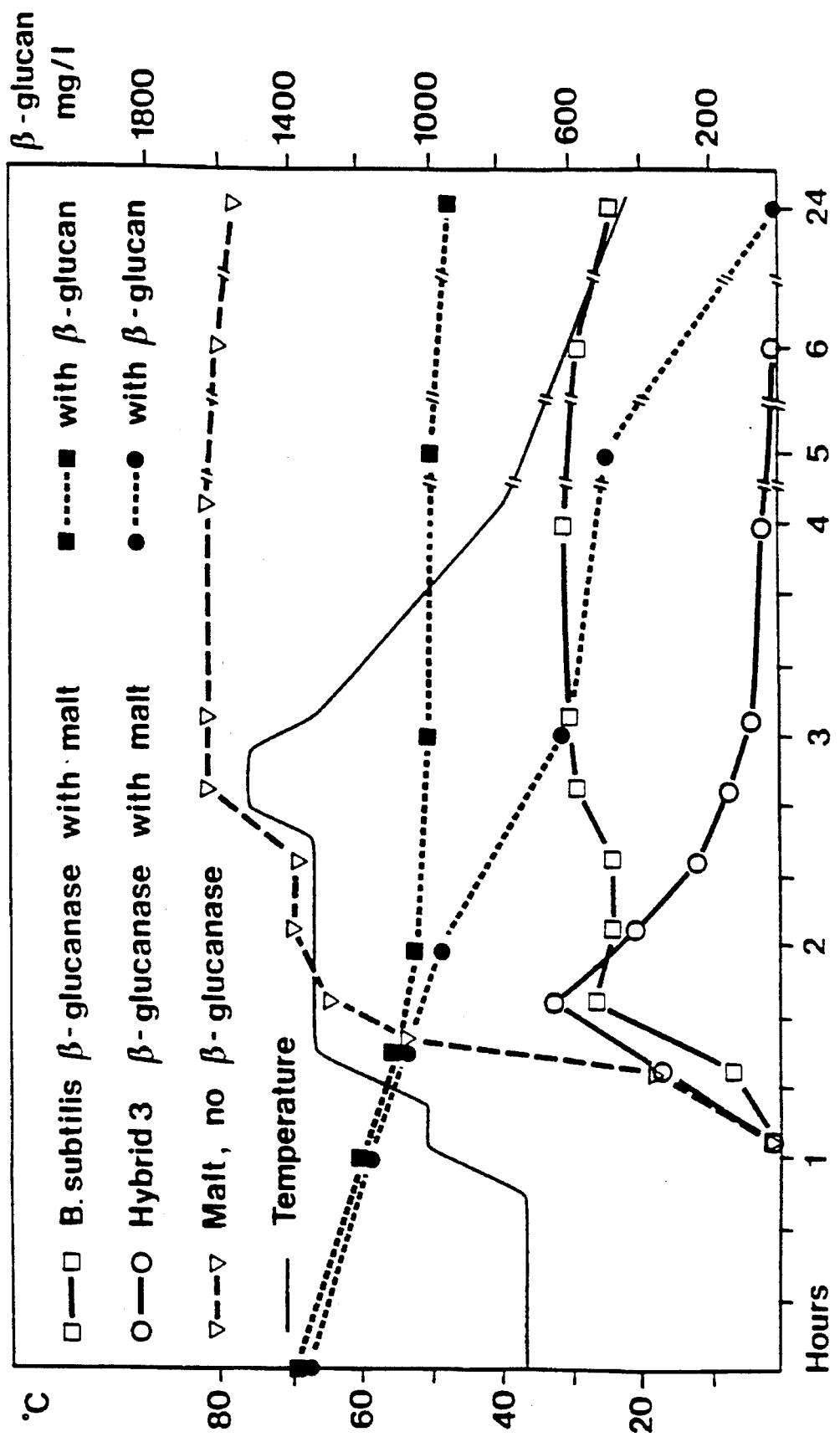

FIG. 15. The concentration of residual malt β-glucans during mashing of mixtures consisting of 50 g finely ground malt and 200 ml water and containing 5 μg H3 hybrid β-glucanase, 5 μg B. subtilis β-glucanase and no β-glucanase, respectively, and of residual β-glucan in solutions consisting of 50 ml β-glucan solutions (1.5 mg/ml) in 100 ml Na-acetate buffer, pH 5.5, 5 mM $CaCl_2$ to which 250 ng B. subtilis β-glucanase and H3 hybrid glucanase, respectively, were added. Samples were drawn periodically and assayed for residual β-glucans.

MATERIALS AND METHODS

Strains, Plasmids and Growth Media

E. coli DH5α cells: F$^-$, endA1, hsd R17 ($r_k^-$, $m_k^+$), supE44, thi1, λ$^-$, recA1, gyrA96, relA1, ø80dlacZ, ΔM15 (Hanahan, 1985) were used for propagation of plasmids and for expression of β-glucanase genes. The vectors comprised pBR322 (Bolivar et al., 1977) and pUC19 (Yanish Perron et al., 1985). The recombinant plasmid pEG1 (Borriss et al., 1985) carries an insert with the B. amyloliquefaciens β-glucanase gene and pUC13-M carries a DNA insert with the β-glucanase gene from B. macerans which is identical to the insert of plasmid pUC19/34 (Borriss et al., 1988). Media and growth conditions were as described previously (Borriss et al., 1988).

Enzymes and Chemicals

Radioactive nucleotides were from New England Nuclear, Boston, Mass., USA. Restriction endonucleases, calf intestinal phosphatase and T4-DNA ligase were from Boehringer Mannheim, Mannheim, W. Germany. Modified T7-DNA polymerase (Sequenase™) was from United States Biochemical Corporation, Cleveland, Ohio, USA. A Geneclean™ kit was from BIO 101 Inc., La Jolla, Calif., USA. Barley β-glucan as well as a β-glucanase assay kit was purchased from Biocon, Boronia, Victoria, Australia. Lichenan was prepared from Cetraria islandica as described previously (Borriss, 1981).

Transformation

E. coli cells were grown and prepared for transformation as described by Lederberg and Cohen (1974) and the competent cells were stored frozen as described by Thomsen (1983).

DNA Purification

Plasmid DNA was prepared from E. coli by the method of Hattori and Sakaki (1986). Specific DNA fragments generated by restriction endonuclease digestion were separated by agarose gel electrophoresis and purified from the gel matrix using a Geneclean™ kit according to the manufacturer's recommendations.

DNA Sequence Determination

Modified T7-DNA polymerase (Sequenase™) was used for nucleotide sequence determination around splice junctions of hybrid-β-glucanase genes. The reactions were performed as described by Zhang et al. (1988).

Enzyme Purification and Analysis

For determination of thermostability of the hybrid enzyme H1 and parental enzymes E. coli cells harbouring the plasmid pUC13-H1, the plasmids pEG1 and pUC13-M were grown in tryptone-yeast medium (10 g tryptone, 5 g yeast extract, 5 g NaCl per 1) at 37° C. for 16 to 20 hours. The cells were lysed by sonication (MSE sonifier) and after clearing of the lysate by centrifugation, β-glucanase stability was analyzed by incubation of the reaction mixture containing an aliquot of clarified lysate for various lengths of time at 65° C. or 70° C. followed by determination of residual β-glucanase activity.

Purification of β-glucanase from cell extracts as described in Borriss et al. (1988) has been used for the parental enzymes and hybrid enzyme H1. Due to low yield of H2 β-glucanase this enzyme was not purified to homogeneity. Ammonium sulphate precipitation of crude cell extracts enriched this β-glucanase to a specific activity of 10.4 U/mg (10.4 μmole glucose mg$^{-1}$·min$^{-1}$). Protein concentration was determined according to Bradford (1976) using bovine serum albumin as standard. Enzyme preparations were analyzed by SDS-PAGE (Laemmli, 1970).

β-Glucanase Assays

Method A: The reaction mixture consisted of 1 ml 0.5% (w/v) lichenan or barley β-glucan in 40 mM Na-acetate buffer, pH 6.0, with or without 10 mM $CaCl_2$. The reaction was initiated by addition of 0.1 ml enzyme solution and incubation was at 37° C. for 20 min. The reaction was stopped by addition of 0.5 ml 3,5-dinitrosalicylic acid and the amount of reducing sugars were measured using the reagent formulation outlined by Miller (1959). Specific activity is expressed as μmole glucose released per min. and mg of protein.

Method B: Alternatively, azo-barley β-glucan was used as substrate for analysis of β-glucanase activity (McCleary, 1988). The buffers employed were: 40 mM sodium acetate, pH 3.6–5.6; 40 mM potassium-sodium phosphate, pH 6–8; 40 mM Tris-HCl, pH 8.4–8.8.

Plate Assay

E. coli cells were incubated on solid medium containing 0.2% (w/v) lichenan. Staining with 0.2% (w/v) Congo red reveals a clearing zone around colonies expressing β-glucanase.

Containment

All experiments involving recombinant DNA were carried out under BL1 laboratory conditions and waste containing biological material was autoclaved.

EXAMPLE 1

CONSTRUCTION OF PLASMIDS pUC13-H1 AND pUC19-H2 CARRYING HYBRID β-GLUCANASE GENES

The B. amyloliquefaciens and B. macerans β-glucanase genes, and proteins, are highly homologous. In the center of the genes is a unique EcoRV restriction site which was used as fusion point in the construction of hybrid β-glucanase genes.

Construction of pUC13-H1 (FIG. 1)

An EcoRV fragment which contains the 5'-flanking region and the amino-terminal half coding region of the B. amyloliquefaciens β-glucanase gene was isolated from plasmid pEG1 (Borriss et al., 1985) and ligated with the large EcoRV-EcoRI fragment from pUC13-M encoding the carboxyl-terminal half of the B. macerans enzymes thus generating plasmid pUC13-H1 carrying the hybrid gene bgl-H1. E. coli DH5α cells transformed with pUC13-H1 are resistant to ampicillin.

Construction of pUC19-H2 (FIG. 2)

For construction of the reciprocal recombinant gene, the B. macerans β-glucanase gene was excised as an EcoRI-PstI fragment from plasmid pUC13-M and recloned in pBR322 giving rise to plasmid pBR-MAC1 from which the small EcoRV fragment was purified and fused to the large EcoRV fragment from plasmid pEG1. With the insert in the correct orientation the plasmid is designated pEG-H2 and E. coli cells transformed with the plasmid were selected on medium containing tetracycline. The hybrid gene was excised from pEG-H2 as an EcoRI-BglII fragment and recloned in EcoRI-BamHI digested pUC19 to give plasmid pUC19-H2.

EXAMPLE 2

THE STRUCTURE OF HYBRID β-GLUCANASE GENES bgl-H1 AND bglH2

The fragment for the expression of the bgl-H1 recombinant gene is shown in FIG. 3. The construct contains 469 bp of the flanking region, 75 bp encoding the signal peptide, and 321 bp encoding the amino-terminal half of the B. amyloliquefaciens β-glucanase. This 865 bp DNA stretch is fused in frame to the carboxyl-terminal half coding region as well as 54 bp of the 3'-flanking region of the β-glucanase gene from B. macerans.

TABLE I

Nucleotide sequence (SEQ ID NO: 1) of the bgl-H1 gene and derived amino acid sequence (SEQ ID NO: 2) of the hybrid pre-β-glucanase consisting of the signal peptide and the amino-terminal of the *B. amyloliquefaciens* β-glucanase and the carboxyl-terminal half of the *B. macerans* β-glucanase. The EcoRV site used for splicing is indicated. An arrow indicates the signal peptidase cleavage site.

```
EcoRI                30                         60                          90
GAATTCAACGAAGAATCGCTGCACTATTATCGATTCGTCACCCACTTAAAGTTTTTCGACCAGCGTCTTTTTAACGGCACACACATGGAA 120                        150                         180
AGCCAGGACGATTTTTTACTGGAGACAGTGAAAGAAAAAGTATCATCAGGCGTATAAATGCACGAAGAATATCCATACCTACATTGAGAAA 210                        240                         270
GAGTATGGGCATAAGCTCACCAGTGACGAGCTGCTGTATTTAACGATTCACATAGAAAAGGGTAGTCAAACAAGTATAATGAAAGCGCTTT 300                        330                         360
CCTCGTATTAATTGTTCTTCCATTCATATATAGGATTGTTACGGATAAAGCAGGCAAAACCTATCTGTGTCGTGATGGTAGTTTAGG 390                        420                         450
TTTGTATTTTTAACAGAAGGATTATCATTATTTCGACCGATGTTCCCTTTGAAAAGGATCATGTATGATCAATAAAGAAAGCGTGTTCAA 480                        510                         540
AAAAGGGGAATGCTAACATGAAACGAGTGTTGCTAATTCTTGTCACCGGATTGTTTATGAGTTTGTGTGGAATCACTTCTAGTGTTTCG
                   Met Lys Arg Val Leu Leu Ile Leu Val Thr Gly Leu Phe Met Ser Leu Cys Gly Ile  Thr  Ser  Ser  Val  Ser 570                        600                         630
GCTCAAACAGGCGGATCGTTTTTTGAACCTTTTAACAGCTATAACTCCGGGTTATGGCAAAAAGCTGATGGTTACTCAAATGGAGATATG
Ala Gln Thr Gly Gly Ser Phe Phe Glu Pro Phe Asn Ser Tyr Asn Ser Gly Leu Trp Gln Lys Ala Asp Gly Tyr Ser Asn Gly Asp Met
   ↑

660                        690                         720
TTTAACTGCACTTGGCGTGCTAATAACGTCTCTATGACGTCATTAGGTGAAATGCGTTTGGCGCTGACAAGTCCGTCTTATAACAAGTTT
Phe Asn Cys Thr Trp Arg Ala Asn Asn Val Ser Met Thr Ser Leu Gly Glu Met Arg Leu Ala Leu Thr Ser Pro Ser Tyr Asn Lys Phe 750                        780                         810
GACTGCGGGGAAAAACCGCTCGGTTCAAACATATGGCTATGGACTTTATGAAGTCAGAATGAAACCGGCTAAAAACACACAGGGATTGTTCA
Asp Cys Gly Glu Asn Arg Ser Val Gln Thr Tyr Gly Tyr Gly Leu Tyr Glu Val Arg Met Lys Pro Ala Lys Asn Thr Gly Ile Val Ser

840                      EcoRV 870                      900
TCGTTCTTCACTTATACAGGTCCAACGGAGGGGACTCCTTGGGATGAGATTGATATCGAATTTCTAGGAAAAGACACGACAAAAGTCCAG
Ser Phe Phe Thr Tyr Thr Gly Pro Thr Glu Gly Thr Pro Trp Asp Glu Ile Asp Ile Glu Phe Leu Gly Lys Asp Thr Thr Lys Val Gln 930                        960                         990
TTTAACTATTATACCAATGGGGTTGGCGGTCATGAAAGGTTATCTCTCTTGGCTTGATGCATCAAAGGGCTTCCATACCTATGCTTTC
Phe Asn Tyr Tyr Thr Asn Gly Val Gly Gly His Glu Lys Val Ile Ser Leu Gly Phe Asp Ala Ser Lys Gly Phe His Thr Tyr Ala Phe
```

TABLE I-continued

Nucleotide sequence (SEQ ID NO: 1) of the bgl-H1 gene and derived amino acid sequence (SEQ ID NO: 2) of the hybrid pre-β-glucanase consisting of the signal peptide and the amino-terminal of the *B. amyloliquefaciens* β-glucanase and the carboxyl-terminal half of the *B. macerans* β-glucanase. The EcoRV site used for splicing is indicated. An arrow indicates the signal peptidase cleavage site.

```
                1020                                    1050                                     1080
GATTGGCAGCCAGGGTATATTAAATGGTATGTAGACGGTGTTTGAAACATACCGCCACCGCGAATATTCCGAGTACGCCAGGCAAAATT
Asp Trp Gln Pro Gly Tyr Ile  Lys Trp Tyr Val Asp Gly Val Leu Lys His Thr Ala Thr Ala Asn Ile  Pro Ser Thr Pro Gly Lys Ile
                1110                                    1140                                     1170
ATGATGAATCTATGGAACGGAACCGGAGTGGATGACTGGTGGATGACTGGTTCTTATAATGGAGCGAATCCGTTGTACGCTGAATATGACTGGGTA
Met Met Asn Leu Trp Asn Gly Thr Gly Val Asp Asp Trp Leu Gly Ser Tyr Asn Gly Ala Asn Pro Leu Tyr Ala Glu Tyr Asp Trp Val
                1200                                    1230     Hind III
AAATATACGAGCAATTAATATGATTGCAGCTGGGCATGAGCTTTTTAGTCCACTCCAGGCATGCAAGCTT
Lys Tyr Thr Ser Asn
```

The other recombinant gene, bgl-H2, (FIG. 4) consists of 99 bp of the 5'-flanking region, 75 bp encoding the signal peptide and 315 bp encoding the amino-terminal half of the *B. macerans* β-glucanase. This 489 bp fragment is fused in frame to a 321 bp DNA segment encoding the carboxyl-terminal half of *B. amyloliquefaciens* β-glucanase and approximately 1.5 Kb 3'-flanking region.

Plasmid constructions were analyzed by restriction enzyme digests, DNA sequence determination around splice junctions, or both.

TABLE II

Nucleotide sequence (SEQ I.D. NO: 3) of the bgl-H2 gene and derived amino acid sequence (SEQ I.D. NO: 4) of the hybrid pre-β-glucanase consisting of the signal peptide and the amino-terminal half of the *B. macerans* β-glucanase and the carboxyl-terminal half of the *B. amyloliquefaciens* protein. The EcoRV site used for splicing is indicated. An arrow indicates the signal peptidase cleavage site. The sequence of the 3' non-coding region is not shown

```
EcoRI                  30                    60                    90
GAATTCCAGCTCGGATATACTATAATTACCCAGGTAAAATATTCCAACACCGTGGCTCCATAACTTCGTTCATATTTAAAATCATTTTGG 120                   150                   180
AGGTGTATTATGAAAAAGAAGTCCTGTTTTACACTGGTGACCACATTTGCGTTTCTTTGATTTTTTCTGTAAGCGCTTTAGCGGGAGT
               Met Lys Lys Lys Ser Cys Phe Thr Leu Val Thr Phe  Ala Phe Ser Leu Ile  Phe Ser Val Ser Ala Leu Ala Gly Ser
                                                                                                              ↑
             210                   240                   270
GTGTTCTGGGAACCATTAAGTTATTTTAATCCGAGTACATGGGAAAAGGCAGATGGGTATTCCAATGGGGGGTGTTCAATTGCACATGG
Val Phe Trp Glu Pro Leu Ser Tyr Phe Asn Pro Ser Thr Trp Glu Lys Ala Asp Gly Tyr Ser Asn Gly Gly Val Phe Asn Cys Thr Trp 300                   330                   360
CGTGCCAACAATGTTAATTTTACGAATGATGGAAAGCTCAAGCTGGGCTTAACGAGTTCTGCGTACAACAAATTTGACTGCGCGGAGTAC
Arg Ala Asn Asn Val Asn Phe Thr Asn Asp Gly Lys Leu Lys Leu Gly Leu Thr Ser Ser Ala Tyr Asn Lys Phe Asp Cys Ala Glu Tyr 390                   420                   450
CGATCAACGAACATTTACGGATACGGCCTGTACGAGGTCAGTATGAAGCCAGCAAAAATACAGGAATTGTCTCATCCTTTTCACGTAT
Arg Ser Thr Asn Ile Tyr Gly Tyr Gly Leu Tyr Glu Val Ser Met Lys Pro Ala Lys Asn Thr Gly Ile  Val Ser Ser Phe Phe Thr Tyr

480       EcoRV        510                   540
ACAGGACCTGCTCATGGCACACAATGGGATGAATATCGAATTTTGGGAAAAGACACAACGAAGGTTCAATTTAACTATTATACA
Thr Gly Pro Ala His Gly Thr Gln Trp Asp Glu Ile  Asp Ile  Glu Phe Leu Gly Lys Asp Thr Thr Lys Val Gln Phe Asn Tyr Tyr Thr 570                   600                   630
AATGGCGCAGGAAACCATGAGAAGTTCGCGGATCTCGGATTTGATGCAGCCAATGCCTATCATACGTATGCGTTCGATTGCCAGCCAAAC
Asn Gly Ala Gly Asn His Glu Lys Phe Ala Asp Leu Gly Phe Asp Ala Ala Asn Ala Tyr His Thr Tyr Ala Phe Asp Trp Gln Pro Asn 660                   690                   720
TCTATTAAATGGTATGTCGATGGGCAATTAAAACATACTGCAACAACCCAAATACCGGCAGCCGCGGGGAAAATCATGAATTTGTGG
Ser Ile  Lys Trp Tyr Val Asp Gly Gln Leu Lys His Thr Ala Thr Thr Gln Ile  Pro Ala Ala Pro Gly Lys Ile  Met Met Asn Leu Trp 750                   780                   810
AATGGTACGGGTGTTGATGATTGGCTCGGTTCCTACAATGGCGTAAATCCGATATACGCTCATTACGACTGGATGCGCTATAGAAAAAAA
Asn Gly Thr Gly Val Asp Asp Trp Leu Gly Ser Tyr Asn Gly Val Asn Pro Ile  Tyr Ala His Tyr Asp Trp Met Arg Tyr Arg Lys Lys 840                   870                                2300
TAATGTACAGAAAAGGATTTCGCTGGCGAATCCTTTTTTGATTAAAACGAAATAATCCC.............................AGATCT
                                                                                            BglII
```

EXAMPLE 3

ANALYSIS OF HYBRID GENE PRODUCTS ENCODED BY pUC13-H1 AND pUC19-H2

*E. coli* DH5α cells were transformed with pUC13-H1 or pUC19-H2, respectively and transformed hybrid β-glucanase genes were expressed in these *E. coli* cells. The hybrid β-glucanase H1 was purified according to the procedure used for *B. macerans* β-glucanase (Borriss et al., 1988). By SDS-PAGE it was confirmed that the β-glucanase migrated as one Coomassie blue staining band (FIG. 5). The yield of hybrid enzyme H2 was only 1% of that obtained of H1 and too low to produce a chromatographically pure preparation (Table III).

TABLE III

Expression of β-glucanase in *E. coli* cells transformed with pUC13-H1 and pUC19-H2, respectively β-glucanase activity (μmole glucose ml culture$^{-1}$·min$^{-1}$)

| Plasmid | Cells | Supernatant |
|---|---|---|
| pUC13-H1 | 67.5 | 7.0 |
| pUC19-H2 | 0.06 | n.d. | n.d. = not detectable

Cells were grown in tryptone-yeast medium with intensive shaking for 20 h at 37° C. After centrifugation (5000×g, 10 min.), the supernatant was used directly for assay of enzyme activity. The pellet was washed, resuspended in 40 mM acetate, pH 6 and sonicated on ice 4×20 sec. with a Branson Sonifier and clarified by centrifugation.

The specific activity of β-glucanase H1 was determined to be 3700 μmole glucose mg$^{-1}$·min.$^{-1}$ which is comparable to the specific activity of β-glucanases from Bacillus IMET B376 (1330 μmole glucose mg$^{-1}$·min$^{-1}$) (Borriss et al., 1985) and from *B. macerans* (5030 μmole glucose mg$^{-1}$·min$^{-1}$). For characterization of the bgl-H2 gene product an enriched extract with a specific activity of 10.4 μmole glucose mg$^{-1}$·min$^{-1}$ was used (Table IV)

TABLE IV

Kinetic parameters of hybrid and parental β-glucanases

| | β-glucanase | | | |
|---|---|---|---|---|
| Substrate | Hybrid 1 | Hybrid 2 | Macerans | Amyloliquefaciens |
| | Relative $V_{max}$ | | | |
| Glucan | 1 | 1 | 1 | 1 |
| Lichenan | 0.77 | 0.88 | 0.73 | 1.1 |
| | $K_m$(mg/ml) | | | |
| Glucan | 1.25 | 1.67 | 0.83 | 1.25 |
| Lichenan | 1.05 | 1.54 | 0.67 | 1.67 |
| | Specific activity μmole glucose mg$^{-1}$·min$^{-1}$ | | | |
| | 3722 | 10.4 (1) | 5030 | 1330 (2) |

(1) enriched cell extract
(2) Borriss and Zemek, 1981

Substrate Specificity

Hybrid enzymes H1 and H2 degraded barley (1,3-1,4)-β-glucan as well as lichenan and the $V_{max}$ values determined with both substrates did not differ significantly (Table IV).

The $K_m$ values for both hybrid proteins were determined using either barley β-glucan or lichenan as substrate.

Kinetics of Thermoinactivation of Hybrid β-Glucanases

The thermostability of hybrid β-glucanases in comparison with the parental enzymes from *B. amyloliquefaciens* and *B. macerans* was studied by measuring the time course of thermoinactivation of β-glucanase in samples of cleared lysates of *E. coli* DH5α cells transformed with plasmids pUC13-H1, pEG-H2, pEG1 and pUC13-M encoding H1, H2, *B. amyloliquefaciens* and *B. macerans* recombinant β-glucanase, respectively.

The *E. coli* strain transformed with pUC13-H1 was deposited with Deutsche Sammlung von Mikroorganismen under the Accession No. DSM 5461. The *E. coli* strain transformed with pEG-H2 was deposited with Deutsche Sammlung von Mikroorganismen under the Accession No. DSM 5460. The *E. coli* strain transformed with pEG1 was deposited with Deutsche Sammlung von Mikroorganismen under the Accession No. DSM 5459 and the *E. coli* strain transformed with pUC13-M was deposited with Deutsche Sammlung von Mikroorganismen under the Accession No. DSM 5462.

The samples (usually in the concentration range 0.3–1 mg protein/ml) were incubated in 10 mM CaCl$_2$, 40 mM Na-acetate, pH 6.0 at 70° C. and samples were removed periodically for determination of residual β-glucanase activity (FIG. 6). The results of this analysis revealed that the half-life of H1 β-glucanase is significantly higher (50% inactivation in 18.5 min.) than half-lives of the parental enzymes from *B. amyloliquefaciens* (4 min.) and *B. macerans* (9 min.). The H2 β-glucanase underwent thermoinactivation with a half-life less than 2 min. and is thus more heat-labile than the parental enzymes. When the analysis was carried out at 65° C. (FIG. 7) the hybrid enzyme H1 was stable for more than 30 min. while the half-life of the enzyme from *B. amyloliquefaciens* was about 25 min. and that of *B. macerans* intermediate between the two. Purified H1 enzyme was stable for more than 1 hour when analyzed at 65° C., pH 6.0, whereas partially purified H2 enzyme was irreversibly thermoinactivated within 20–25 min. (FIG. 8). A time course for the inactivation of purified enzyme from *B. amyloliquefaciens* is shown as reference. Consistently, the hybrid enzyme H1 was significantly activated when tested after 5 min. at 65° to 70° C. (FIGS. 6–8).

Effect of pH on Enzymatic Activity and Stability of Hybrid β-Glucanases

The pH range for optimal enzymatic activity of hybrid β-glucanase H1 was pH 5.6 to 6.6, while that for hybrid enzyme H2 was pH 7.0 to 8.0 (FIG. 9). For comparison, the pH optimum range for enzymatic activity of the β-glucanases from *B. amyloliquefaciens* and *B. macerans* was from pH 6.0 to 7.0 and from pH 6.0 to 7.5, respectively (results not shown). FIG. 9 also shows that the hybrid enzyme H1 retains 50% of its activity at pH 4.8 and that H2 retains 50% of its activity at pH 5.6. The corresponding values for the parental enzymes are pH 5.2 (*B. amyloliquefaciens*) and pH 5.5 (*B. macerans*).

Another characteristic is enzyme stability as a function of pH. When the time course of thermoinactivation of the β-glucanases in crude extracts was followed at pH 4.0 and a temperature of 65° C. the hybrid enzyme H1 was stable for more than 30 min. while the β-glucanase from *B. amy-*

*loliquefaciens* had a half-life of 20 min. and that of *M. macerans* of only 12 min. (FIG. 10). This feature was examined for hybrid and parental β-glucanases by incubation at 55° C. for 1 h in the range pH 3 to 9, followed by determination of residual enzymatic activity (FIG. 11). It appears that β-glucanase H1 is stable from below pH 3.6 up to 7.0, while β-glucanase H2 has a very narrow pH range of stability between pH 5.6 to 6.0. Both parental β-glucanases are unstable below pH 4.8 and above pH 6.0 (*B. amyloliquefaciens*) or pH 6.5 (*B. macerans*).

The Effects of $Ca^{++}$ on Thermostability

The effect of $Ca^{++}$ on the stability of hybrid β-glucanases was analyzed in a 30 min. assay at pH 5.5 and temperatures ranging from 45° C. to 75° C. From the results of this analysis, shown in FIG. 12, the temperature for 50% inactivation in a 30 min. assay can be deduced. It appears clearly that $Ca^{++}$ ions have a stabilizing effect on both hybrid enzymes. The temperatures for 50% inactivation increase about 5° C. for both hybrid β-glucanases in the presence of 10 mM $Ca^{++}$. The same stabilizing effect of $Ca^{++}$ ions is also found for the two parental enzymes.

EXAMPLE 4

CONSTRUCTION OF HYBRID β-GLUCANASES H3, H4, H5, AND H6

Four (1,3-1,4)-β-glucanases were produced by constructing hybrid fusion genes encoding the glucanases using a polymerase chain reaction technique according to the procedure described by Yon & Fried (1989), Nucleic Acid Res., 17, 4895, and Horton et al. (1989) Gene, 77, 61–68. The fusion genes comprise DNA sequences from the *B. amyloliquefaciens* BE20/78 β-glucanase gene and from the *B. macerans* E 138 β-glucanase gene. The fusion genes were inserted in the plasmid pTZ19R (Mead et al., 1986, Protein Engineering, 1, 67–74). The four resulting recombinant plasmids were designated pTZ19R-H3, pTZ19R-H4, pTZ19R-H5, and pTZ19R-H6, respectively. The plasmids were used for transformation of *E. coli* DH5α. The host cells were grown in minimal medium to stationary phase to obtain expression of the β-glucanase genes. The resulting hybrid enzymes were designated H3, H4, H5, and H6, respectively. The H3 enzyme has the formula A16—M indicating that it is a hybrid enzyme comprising 16 amino acids from the N-terminal part of mature *B. amyloliquefaciens* (1,3-1,4)-β-glucanase which have replaced the corresponding 16 amino acids from the N-terminal part of the mature *B. macerans* (1,3-1,4)-β-glucanase. The hybrid enzymes H4–H6 were constructed in a similar manner by replacing 36, 78, and 152 amino acids, respectively of the N-terminal part of mature *B. macerans* (1,3-1,4)-β-glucanase with the corresponding number of amino acids from the N-terminal part of the *B. amyloliquefaciens* β-glucanase. Thus all of the four constructed hybrid enzymes have an N-terminal end originating from the *B. amyloliquefaciens* (1,3-1,4)-β-glucanase. Furthermore, all hybrid enzymes are synthesized with the transient signal peptide of *B. amyloliquefaciens* β-glucanase.

The *E. coli* strain carrying pTZ19R-H3 encoding the hybrid enzyme H3 has been deposited with Deutsche Sammlung von Mikroorganismen under the Accession No. DSM 5790, the *E. coli* strain transformed with pTZ19R-H4 encoding the hybrid enzyme H4 was deposited with Deutsche Sammlung von Mikroorganismen under the Accession No. DSM 5791, the *E. coli* strain transformed with pTZ19-H5 encoding the hybrid enzyme H5 was deposited with Deutsche Sammlung von Mikroorganismen under the Accession No. DSM 5792, and the *E. coli* strain carrying the pTZ19R-H6 plasmid encoding the hybrid enzyme H6 was deposited with Deutsche Sammlung von Mikroorganismen under the Accession No. DSM 5793. All the above four strains were deposited on 9 Feb., 1990.

EXAMPLE 5

PURIFICATION AND CHARACTERIZATION OF HYBRID β-GLUCANASES H3, H4, H5, AND H6

The hybrid enzymes encoded by the hybrid fusion genes were characterized by determining their temperature optimum, pH optimum, specific activity, and thermostability. These characteristics were compared with the corresponding characteristics of the hybrid enzyme H1 as described hereinbefore and of native Bacillus β-glucanases as produced by the following Bacillus spp.: *B. amyloliquefaciens* BE20/78, *B. macerens* E 138, and a *B. subtilis* sp. *E. coli* cells transformed with plasmids carrying the genes encoding said *B. amyloliquefaciens* β-glucanase (pEG1) and *B. macerans* β-glucanase (pUC13-M), respectively were grown in minimal medium to stationary phase to obtain expression of the β-glucanase gene products.

One to five liters of culture medium resulting from the growth of the above transformed *E. coli* cells expressing the hybrid β-glucanases H3, H4, H5, and H6 and the native *B. amyloliquefaciens* and *B. macerans* β-glucanases were cleared by centrifugation and filtration through an 0.8 μm filter. The cleared supernatants were concentrated to 100 ml by ultrafiltration. Following diafiltration against 20 mM Na-acetate, pH 5.0, 5 mM $CaCl_2$, the crude supernatant was applied to a CM-sepharose cation exchange column. After washing, the column was eluted with 50 mM sodium acetate, pH 5.0, 50 mM NaCl, 5 mM $CaCl_2$. The β-glucanase obtained by this purification scheme was essentially pure, but usually the fractions containing β-glucanase activity were pooled and concentrated to 2–5 ml and subjected to molecular sieve chromatography on a Sephacryl S200 HR column (2.5×60 cm) in 20 mM sodium acetate, pH 5.0, 5 mM $CaCl_2$. The β-glucanase peak fractions were used for analysis of the thermostability of pure enzymes. The yield of pure β-glucanase was in the range of 0.5–25 mg per liter culture medium.

The native *B. subtilis* enzyme was a commercial (1,3-1, 4)-β-glucanase product (Cereflo® 200L, Novo-Nordisk A/S, Bagsværd, Denmark). As a first step of purification this product was concentrated five-fold followed by diafiltration against 50 mM Tris-HCl, pH 8 and anion exchange chromatography (Whatman DE 53). Unbound protein was concentrated and the buffer was changed to 20 mM sodium acetate, pH 5.0, 5 mM $CaCl_2$ by diafiltration. Further purification was obtained by cation exchange chromatography on CM52 (Whatman). Fractions containing β-glucanase activity were pooled, concentrated and subjected to molecular sieve chromatography on Sephacryl S200 HR. Approximately 100 mg pure *B. subtilis* β-glucanase was obtained from 1 liter of Cereflo® 200L.

Temperature Optima for H3–H6

The above pure preparations of the test enzymes and of the reference enzymes containing 100 μg purified enzyme per ml were diluted to contain an amount of enzyme which under the assay conditions resulted in measurable values (0.5–1.5 µg per ml). The reaction mixtures consisted of 1 ml substrate (0.5 mg/ml lichenan) in 100 mM Na-acetate buffer, pH 6.0 supplemented with 50 µg/ml bovine serum albumin and 0.1 ml of the appropriately diluted enzyme preparations. The reaction mixtures were incubated for 10 minutes at the following temperatures: 25°, 37°, 50°, 55°, 60°, 65°, 70°, 75°, 80°, and 85° C. and the reaction was stopped by the addition of 0.5 ml 3,5-dinitrosalicylic acid. The optimum temperatures and the temperature ranges within which at least 90% of the optimum activity was exerted were determined and the results are shown in the below table:

TABLE V

Temperature optima for H3–H6, H1, and native Bacillus β-glucanases

| β-glucanase | Temperature optimum °C. | Temperature range with ≧90% of optimum activity, °C. |
|---|---|---|
| H3 | 65 | 55–75 |
| H4 | 70 | 55–70 |
| H5 | 65 | 55–70 |
| H6 | 55 | 50–65 |
| H1 | 55 | 50–65 |
| B. subtilis | 55 | 50–65 |
| B. macerans | 65 | 60–70 |
| B. amylolique-faciens | 55 | 50–65 |

Additionally, the H3 enzyme had a residual activity at 80° C. of 75% of the optimum activity and at 85° C. the corresponding residual activity was 20%.

Among the tested hybrid enzymes, H4 had a higher temperature optimum than any of the native enzymes (70° C.) and the H3 enzyme showed the broadest temperature range within which 90% or more of the optimum activity was retained (55°–75° C.). This enzyme also had the highest temperature limit for at least 90% activity relative to its optimum activity.

pH Optima for H3–H6

In these experiments the enzymatic activity of the same enzyme preparations as described above including the reference enzymes was assayed at different pH-values ranging from 3.6 to 8.0. In the assay, Azo-barley β-glucan was used as the substrate. 200 µl of substrate solution was mixed with 200 µl 100 mM buffer solutions having appropriate pH-values and containing 10–100 ng of the purified enzyme preparations. Within the pH range 3.6 to 6.0 Na-acetate buffers were used and within the range of 6.1 to 8.0 Tris-acetate were used. The assay time was 10 minutes. The pH optimum and the pH interval within which at least 90% of the optimum activity was present were determined for each enzyme preparation. Furthermore, the activity of the enzymes at pH 5.0 relative to the activity at the optimum pH was calculated. These assay results are summarized in the table below:

TABLE VI pH optima for H3–H6, H1, and native Bacillus β-glucanases

| β-glucanase | pH optimum | pH range with ≧90% of optimum activity | Activity of pH 5.0 relative to to optimum | pH 5.5 |
|---|---|---|---|---|
| H3 | 7.0 | 6.5–7.0 | 10% | 63% |
| H4 | 6.5 | 5.9–7.6 | 15% | 70% |
| H5 | 7.0 | 5.9–7.6 | 30% | 88% |
| H6 | 6.5 | 5.9–6.5 | 50% | 80% |
| H1 | 5.9 | 5.5–6.5 | 55% | 86% |
| B. subtilis | 6.5 | 5.9–6.5 | 19% | 75% |
| B. macerans | 7.6 | 5.9–7.6 | 8% | 56% |
| B. amylolique faciens | 6.5 | 5.9–7.0 | 30% | 69% |

The pH optima for the four test enzymes were in the range of 6.5– 7.0. At pH 5.0 the enzymes H5 and H6 showed activities relative to these at their pH optima which exceeded the corresponding values for all of the three native Bacillus enzymes indicating a somewhat lower sensitivity to non-optimum pH conditions. The lower pH limit for retaining at least 90% activity was 5.9 for all test enzymes which is similar to what was found for the native enzymes. The results of this experiment therefore indicates that by constructing hybrid enzymes comprising polypeptides from the B. amyloliquefaciens and B. macerans (1,3-1,4)-β-glucanase a higher tolerance to acidic conditions can be obtained.

The Specific Activity of H3–H6

The specific activity of the H3–H6 β-glucanases were determined essentially as described hereinbefore using the preparations of purified enzymes at a concentration of 100 µg β-glucanase protein per ml of 20 mM Na-acetate buffer, pH 6.0 supplemented with 5 mM $CaCl_2$. The reaction mixtures were incubated at 25° and 50° C., respectively for 20 minutes after which the specific activity in terms of µmoles glucose released per mg of enzyme per minute was determined. The results are shown in the table below.

TABLE V

Specific activities of H3–H6, H1, and native Bacillus β-glucanases (µmole glucose mg purified enzyme$^{-1}$·min$^{-1}$)

| β-glucanase | Specific activity at | |
|---|---|---|
|  | 25°C. | 50° C. |
| H3 | 790 | 1700 |
| H4 | 850 | 2600 |
| H5 | 615 | 1890 |
| H6 | 2040 | 3750 |
| Hi | 2130 | 3690 |
| B. subtills | 1420 | 2600 |
| B. macerans | 350 | 1180 |
| B. amyloliquefaciens | 1320 | 2490 |

From the results it appears that at 25° C. the hybrid enzyme H6 has a specific activity which is significantly higher than any of the parental Bacillus enzymes and of the B. subtilis β-glucanase. Generally, the specific activities at 50° C. were 1.5–3 times higher than the values at 25° C. Also at this temperature the specific activity of H6 exceeded that of the parental enzymes as well as that of the native Bacillus subtilis β-glucanase. The hybrid enzyme H1 also exhibited a high specific activity at both temperatures of the same magnitude as the H6 enzyme.

The Thermostability of Hybrid β-Glucanases H3–H6

The thermostabilities of the purified hybrid enzymes were determined in comparison with those of the purified native enzymes from the previously mentioned Bacillus spp. essentially according to the procedure described in Example 3. The enzyme activities were tested at 65° C., pH 4.1 and at 70° C., pH 6.0. The concentrations of enzymes were 100 µg/ml of the assay buffer. Samples of the reaction mixtures were collected at time intervals indicated in FIGS. 13 and 14 in which the results are summarized. It appears that the hybrid β-glucanases H3, H4 and H5 in comparison with the native enzymes showed an extremely high stability at 65° C. and at pH 4.1. More than 90% of the initial enzyme activity of H3 and H4 and 85% of H5 remained after 60 minutes. At 70° C. and pH 6.0 the residual enzyme activity of H3 after 60 minutes was 85%. In contrast hereto, the residual activity of the native enzymes after 60 minutes at 65° C. and pH 4.1 was only about 10% for the *B. amyloliquefaciens* and the *B. subtilis* (1,3-1,4)-β-glucanase whereas the *B. macerans* β-glucanase was completely inactivated after 10 minutes. At 70° C. and pH 6.0 less than 10% activity of the *B. subtilis*, the *B. macerans* and the *B. amyloliquefaciens* enzymes remained after 60 minutes of incubation.

EXAMPLE 6

THE EFFECT OF H3 HYBRID (1,3-1,4)-β-GLUCANASE ON THE HYDROLYSIS OF BARLEY β-GLUCAN DURING MASHING

An experiment was carried out in which the efficiency of the H3 hybrid enzyme to degrade barley β-glucan during a mashing process was compared to the efficiency of a commercial β-glucanase product. The mashing mixture consisted of 50 g finely ground malt to which 200 ml of prewarmed (37° C.) tap water was added. To this substrate mixture 5 µg of the purified preparation of H3 enzyme was added under thorough mixing. As controls two similar mashing mixtures were prepared to one of which an amount of the commercial β-glucanase product Cereflo® 200L (Novo-Nordisk A/S) containing 5 µg *Bacillus subtilis* β-glucanase was added. The last mashing mixture served as a negative control without any addition of β-glucanase. The thus prepared mixtures were left at 37° C. for about 50 minutes to initiate mashing whereafter they were heated according to the temperature curve indicated in FIG. 15 until 175 minutes. During the period from 65 to 185 minutes samples were drawn from the mixtures at the intervals indicated in FIG. 15. Subsequent to this period of mashing further samples were drawn after 4, 6, and 24 hours.

The drawn samples were immediately cooled in ice and centrifuged at 40° C. after which the supernatants were transferred to fresh tubes and incubated for 15 minutes in boiling water to inactivate the enzymes. The samples were then assayed for residual β-glucan using calcofluor complex formation and flow injection analysis according to the procedure described by Jørgensen (Carlsberg Res. Commun., 1988, 53, 277– 285 and 287–296.

The results of the mashing experiments are summarized in FIG. 15 which shows the amounts of residual β-glucans in the above mashing mixtures. It appears clearly that the addition of β-glucanases resulted in significantly lower amounts of β-glucans in the mixtures as compared to the negative control. Whereas the commercial β-glucanase product ceased to hydrolyze further β-glucan when the temperature exceeded about 67° C. the hybrid enzyme H3 added at the same concentration continuously degraded β-glucans during the whole incubation period irrespective of the temperature conditions. The H3 enzyme was so active that the amount of residual β-glucans after the termination of the mashing process was less than 100 mg per liter as compared to about 1600 mg in the negative control mixture and about 600 mg per liter of the mixture with the commercial *B. subtilis* β-glucanase. After 24 hours of mashing and standing essentially no detectable residual β-glucans were found in the mixture to which the H3 hybrid enzyme has been added.

During the same experiment the amounts of residual β-glucans were analyzed in solutions of pure β-glucans to which was added 250 µg of H3 hybrid β-glucanase and *B. subtilis* β-glucanase, respectively. The solutions consisted of 50 ml β-glucan (1.5 mg/ml) in 100 mM Na-acetate, pH 5.5, 5 mM $CaCl_2$. The solutions were prewarmed to 37° C. before addition of the enzymes.

REFERENCES

Argos, P., M. G. Rossmann, V. M. Grau, H. Zuber & J. D. Tratschin (1979): Thermal stability and protein structure. Biochemistry 18, 5698–5703.

Bolivar, F., R. L. Rodriguez, P. J. Greene, M. C. Betlach, H. L. Heyneker, H. W. Boye (1977): Construction and characterization of new cloning vehicle. II. A multipurpose cloning system. Gene 2, 95–113.

Borriss, R. (1981): Purification and characterization of an extracellular beta-glucanase from Bacillus IMET B376. Z. Alg. Mikrobiologie 21, 7–17.

Borriss, R. & K. L. Schroeder (1981): β-1,3-1,4-glucanase in sporeforming microorganisms. V. The efficiency of β-glucanase in reducing the viscosity of wort. Zbl. Bakt. II Abt. 136, 324–329.

Borriss, R., H. Bäumlein & J. Hofemeister (1985): Expression in *Escherichia coli* of a cloned β-glucanase gene from *Bacillus amyloliquefaciens*. Appl. Microbiol. Biotechnol. 22, 63–71.

Borriss, R., R. Manteuffel & J. Hofemesiter (1988): Molecular cloning of a gene coding for thermostable beta-glucanase from *Bacillus macerans*. J. Basic Microbiol. 28, 3–10.

Bradford, M. M (1976): A rapid and sensitive method for the quantitation of microgram quantities of protein utilizing the principle of protein dye binding. Anal. Biochem. 72, 248–254.

Cantwell, B. A. & D. J. McConnell (1983): Molecular cloning and expression of a *Bacillus subtilis* β-glucanase gene in *Escherichia coli*. Gene 23, 211–219.

DD Patent Application WP c12N/315 706 1, corresponds to DD patent No. 272102.

Godfrey, T. (1983): On comparison of key characteristics of industrial enzymes by type and source. Godfrey, T. & J. Reichelt (eds) Industrial Enzymology. MacMillan, London, p. 466.

Hanahan, D. (1985): Techniques for transformation of *E. coli*. In: DNA Cloning, vol. 1. A practical approach. D. M. Glover ed., IRL Press, Oxford, pp. 109–135.

Hattori, M. & Y. Sakaki (1986): Dideoxy sequencing method using denatured plasmid templates. Anal. Chem. 152, 232–238.

Hofemeister, J., A. Kurtz, R. Borriss & J. Knowles (1986): The β-glucanase gene from *Bacillus amyloliquefaciens* shows extensive homology with that of *Bacillus subtilis*. Gene 49, 177–187.

Horton, R. M., H. D. Hunt, S. N. Ho, J. K. Pullen & L. R. Pease (1989): Engineering hybrid genes without the use of restriction enzymes: Gene splicing by overlap extension. Gene 77, 61–68.

Imanaka, T., M. Shibazaki & M. Takagi (1986): A new way of enhancing the thermostability of proteases. Nature 324, 695–697.

Jørgensen, K. G. et al. (1988): Quantification of high molecular weight (1→3)(1→4)-β-D-glucan using calcofluor complex formation and flow injection analysis. I. Analytical principle and its standardization. Carlsberg Res. Commun. 53, 277–285.

Jørgensen, K. G. et al. (1988): Quantification of high molecular weight (1→3)(1→4)-β-D-glucan using calcofluor complex formation and flow injection analysis. II. Determination of total β-glucan content of barley and malt. Carlsberg Res. Commun. 53, 287–296.

Laemmli, U. K. (1970): Cleavage of structural proteins during the assembly of the head of bacteriophage T4. Nature 227, 680–685.

Lederberg, E. M. & S. N. Cohen (1974): Transformation of *Salmonella typhimurium* by plasmid deoxyribonucleic acid. J. Bacteriol. 119, 1072–1074.

Loi, L., P. A. Barton & G. B. Fincher (1987): Survival of barley (1→3,1→4)-β-glucanase isoenzymes during kilning and mashing. J. Cereal Sci. 5, 45–50.

Matthews, B. W., H. Nicholson & W. J. Becktel (1987): Enhanced protein thermostability from site-directed mutations that decrease the entropy of unfolding. Proc. Natl. Acad. Sci. 84, 6663–6667.

McCleary, B. V. (1988): Soluble, dye-labeled polysaccharides for the assay of endohydrolases. Methods Enzymol. 160, 74–86.

McFadden, G. I., B. Ahluwalia, A. E. Clarke & G. B. Fincher (1988): Expression sites and developmental regulation of genes encoding (1→3,1→4)-β-glucanases in germinated barley. Planta 173, 500–508.

Mead, B. A., E. Szczesna-Skorupa & B. Kemper (1986): Single-stranded DNA "blue" T7 promoter plasmids: A versatile tandem promoter system for cloning and protein engineering. Protein engineering, 1, 67–74.

Merrifield, R. B. (1963). J. Am. Chem. Soc. 85, p. 2149.

Miller, G. L. (1959): Use of dinitrosalicylic acid reagent for determination of reducing sugars. Analytical Chemistry 31, 426–428.

Murphy, N., D. J. McConnell & B. A. Cantwell (1984): The DNA sequence of the gene and genetic control sites for the excreted *B. subtilis* enzyme β-glucanase. Nucleic Acids Res. 12, 5355–5367.

Querol, E. & A. Parilla (1987): Tentative rules for increasing the thermostability of enzymes by protein engineering. Enzyme Microb. Technol. 9, 238–244.

Shinnick (1983). Ann. Rev. Microbiol. 37, 425–446.

Streuli, M., A. Hall, W. Boll, W. E. Stewart II, S. Nagata & C. Weissmann (1981): Target cell specificity of two species of human interferon-alpha produced in *Escherichia coli* and of hybrid molecules derived from them. Proc. Natl. Acad. Sci. USA, 2848–2852.

Thomsen, K. K. (1983): Mouse α-amylase synthesized by *Saccharomyces cerevisiae* is released into the culture medium. Carlsberg Res. Commun. 48, 545–555.

Yanish-Perron, C., J. Vieira & J. Messing (1985): Improved M13 phage cloning vectors and host strains: nucleotide sequences of the M13 mp18 and pUC19 vectors. Gene 33, 103–119.

Weck, P., T. Apperson, N. Stebbing, H. M. Shephard, D. V. Goeddel (1981): Antiviral activities of hybrids of two major human leukocyte interferons. Nucleic Acids Res. 9, 6153–6165.

Yon, J. & M. Fried (1989): Precise gene fusion by PCR. Nucleic Acid Res. 17, 4895.

Zhang, H., R. Scholl, J. Browse & C. Sommerville (1988): Double stranded sequencing as a choice for DNA sequencing. Nucleic Acids Res. 16, 1220.

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1240 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bacillus ( i x ) FEATURE:
        ( A ) NAME/KEY: CDS
        ( B ) LOCATION: 469..1185

( x i ) SEQUENCE DESCRIPTION: SEQ ID NO:1:

-continued

```
GAATTCAACG AAGAATCGCT GCACTATTAT CGATTCGTCA CCCACTTAAA GTTTTTCGAC       60

CAGCGTCTTT TTAACGGCAC ACACATGGAA AGCCAGGACG ATTTTTTACT GGAGACAGTG      120

AAAGAAAAGT ATCATCAGGC GTATAAATGC ACGAAGAATA TCCATACCTA CATTGAGAAA      180

GAGTATGGGC ATAAGCTCAC CAGTGACGAG CTGCTGTATT TAACGATTCA CATAGAAAGG      240

GTAGTCAAAC AAGTATAATG AAAGCGCTTT CCTCGTATTA ATTGTTTCTT CCATTCATAT      300

ATAGGATTGT TACGGATAAA GCAGGCAAAA CCTATCTGTC TGTGCTGATG GTAGTTTAGG      360

TTTGTATTTT TAACAGAAGG ATTATCATTA TTTCGACCGA TGTTCCCTTT GAAAGGATC      420

ATGTATGATC AATAAGAAA GCGTGTTCAA AAAGGGGGA ATGCTAAC ATG AAA CGA        477
                                                     Met Lys Arg
                                                      1

GTG TTG CTA ATT CTT GTC ACC GGA TTG TTT ATG AGT TTG TGT GGG ATC        525
Val Leu Leu Ile Leu Val Thr Gly Leu Phe Met Ser Leu Cys Gly Ile
      5              10                  15

ACT TCT AGT GTT TCG GCT CAA ACA GGC GGA TCG TTT TTT GAA CCT TTT        573
Thr Ser Ser Val Ser Ala Gln Thr Gly Gly Ser Phe Phe Glu Pro Phe
 20              25                  30                      35

AAC AGC TAT AAC TCC GGG TTA TGG CAA AAA GCT GAT GGT TAC TCA AAT        621
Asn Ser Tyr Asn Ser Gly Leu Trp Gln Lys Ala Asp Gly Tyr Ser Asn
                  40                  45                  50

GGA GAT ATG TTT AAC TGC ACT TGG CGT GCT AAT AAC GTC TCT ATG ACG        669
Gly Asp Met Phe Asn Cys Thr Trp Arg Ala Asn Asn Val Ser Met Thr
              55                  60                  65

TCA TTA GGT GAA ATG CGT TTG GCG CTG ACA AGT CCG TCT TAT AAC AAG        717
Ser Leu Gly Glu Met Arg Leu Ala Leu Thr Ser Pro Ser Tyr Asn Lys
          70                  75                  80

TTT GAC TGC GGG GAA AAC CGC TCG GTT CAA ACA TAT GGC TAT GGA CTT        765
Phe Asp Cys Gly Glu Asn Arg Ser Val Gln Thr Tyr Gly Tyr Gly Leu
      85                  90                  95

TAT GAA GTC AGA ATG AAA CCG GCT AAA AAC ACA GGG ATT GTT TCA TCG        813
Tyr Glu Val Arg Met Lys Pro Ala Lys Asn Thr Gly Ile Val Ser Ser
100                 105                 110                 115

TTC TTC ACT TAT ACA GGT CCA ACG GAG GGG ACT CCT TGG GAT GAG ATT        861
Phe Phe Thr Tyr Thr Gly Pro Thr Glu Gly Thr Pro Trp Asp Glu Ile
              120                 125                 130

GAT ATC GAA TTT CTA GGA AAA GAC ACG ACA AAA GTC CAG TTT AAC TAT        909
Asp Ile Glu Phe Leu Gly Lys Asp Thr Thr Lys Val Gln Phe Asn Tyr
          135                 140                 145

TAT ACC AAT GGG GTT GGC GGT CAT GAA AAG GTT ATC TCT CTT GGC TTT        957
Tyr Thr Asn Gly Val Gly Gly His Glu Lys Val Ile Ser Leu Gly Phe
      150                 155                 160

GAT GCA TCA AAG GGC TTC CAT ACC TAT GCT TTC GAT TGG CAG CCA GGG       1005
Asp Ala Ser Lys Gly Phe His Thr Tyr Ala Phe Asp Trp Gln Pro Gly
165                 170                 175

TAT ATT AAA TGG TAT GTA GAC GGT GTT TTG AAA CAT ACC GCC ACC GCG       1053
Tyr Ile Lys Trp Tyr Val Asp Gly Val Leu Lys His Thr Ala Thr Ala
180                 185                 190                 195

AAT ATT CCG AGT ACG CCA GGC AAA ATT ATG ATG AAT CTA TGG AAC GGA       1101
Asn Ile Pro Ser Thr Pro Gly Lys Ile Met Met Asn Leu Trp Asn Gly
              200                 205                 210

ACC GGA GTG GAT GAC TGG TTA GGT TCT TAT AAT GGA GCG AAT CCG TTG       1149
Thr Gly Val Asp Asp Trp Leu Gly Ser Tyr Asn Gly Ala Asn Pro Leu
          215                 220                 225

TAC GCT GAA TAT GAC TGG GTA AAA TAT ACG AGC AAT TAATATGATT            1195
Tyr Ala Glu Tyr Asp Trp Val Lys Tyr Thr Ser Asn
      230                 235
```

GCAGCTGGGC ATGAGCTTTT TAGTCCACTC CAGGCATGCA AGCTT                        1240

( 2 ) INFORMATION FOR SEQ ID NO:2:

( i ) SEQUENCE CHARACTERISTICS:
        ( A ) LENGTH: 239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Lys | Arg | Val | Leu | Leu | Ile | Leu | Val | Thr | Gly | Leu | Phe | Met | Ser | Leu |
|---|---|---|---|---|---|---|---|---|---|---|---|---|---|---|---|
| 1 | | | | 5 | | | | | 10 | | | | | 15 | |
| Cys | Gly | Ile | Thr | Ser | Ser | Val | Ser | Ala | Gln | Thr | Gly | Gly | Ser | Phe | Phe |
| | | | 20 | | | | | 25 | | | | | 30 | | |
| Glu | Pro | Phe | Asn | Ser | Tyr | Asn | Ser | Gly | Leu | Trp | Gln | Lys | Ala | Asp | Gly |
| | | 35 | | | | 40 | | | | | 45 | | | | |
| Tyr | Ser | Asn | Gly | Asp | Met | Phe | Asn | Cys | Thr | Trp | Arg | Ala | Asn | Asn | Val |
| | 50 | | | | 55 | | | | | 60 | | | | | |
| Ser | Met | Thr | Ser | Leu | Gly | Glu | Met | Arg | Leu | Ala | Leu | Thr | Ser | Pro | Ser |
| 65 | | | | | 70 | | | | 75 | | | | | | 80 |
| Tyr | Asn | Lys | Phe | Asp | Cys | Gly | Glu | Asn | Arg | Ser | Val | Gln | Thr | Tyr | Gly |
| | | | 85 | | | | | 90 | | | | | 95 | | |
| Tyr | Gly | Leu | Tyr | Glu | Val | Arg | Met | Lys | Pro | Ala | Lys | Asn | Thr | Gly | Ile |
| | | | 100 | | | | 105 | | | | | 110 | | | |
| Val | Ser | Ser | Phe | Phe | Thr | Tyr | Thr | Gly | Pro | Thr | Glu | Gly | Thr | Pro | Trp |
| | | 115 | | | | | 120 | | | | | 125 | | | |
| Asp | Glu | Ile | Asp | Ile | Glu | Phe | Leu | Gly | Lys | Asp | Thr | Thr | Lys | Val | Gln |
| | 130 | | | | | 135 | | | | 140 | | | | | |
| Phe | Asn | Tyr | Tyr | Thr | Asn | Gly | Val | Gly | Gly | His | Glu | Lys | Val | Ile | Ser |
| 145 | | | | | 150 | | | | 155 | | | | | | 160 |
| Leu | Gly | Phe | Asp | Ala | Ser | Lys | Gly | Phe | His | Thr | Tyr | Ala | Phe | Asp | Trp |
| | | | 165 | | | | | 170 | | | | | 175 | | |
| Gln | Pro | Gly | Tyr | Ile | Lys | Trp | Tyr | Val | Asp | Gly | Val | Leu | Lys | His | Thr |
| | | | 180 | | | | | 185 | | | | | 190 | | |
| Ala | Thr | Ala | Asn | Ile | Pro | Ser | Thr | Pro | Gly | Lys | Ile | Met | Met | Asn | Leu |
| | | 195 | | | | | 200 | | | | | 205 | | | |
| Trp | Asn | Gly | Thr | Gly | Val | Asp | Asp | Trp | Leu | Gly | Ser | Tyr | Asn | Gly | Ala |
| | 210 | | | | | 215 | | | | | 220 | | | | |
| Asn | Pro | Leu | Tyr | Ala | Glu | Tyr | Asp | Trp | Val | Lys | Tyr | Thr | Ser | Asn | |
| 225 | | | | | 230 | | | | | 235 | | | | | |

( 2 ) INFORMATION FOR SEQ ID NO:3:

( i ) SEQUENCE CHARACTERISTICS:
        ( A ) LENGTH: 2300 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bacillus ( i x ) FEATURE:
        ( A ) NAME/KEY: CDS (B) LOCATION: 100..810

(xi) SEQUENCE DESCRIPTION: SEQ ID NO:3:

```
GAATTCCAGC TCGGATATAC TATAATTACC CAGGTAAAAT ATTCCAACAC CGTGGCTCCA        60

TAACTTCGTT CATATTTAAA ATCATTTGG AGGTGTATT ATG AAA AAG AAG TCC           114
                                            Met Lys Lys Lys Ser
                                              1               5

TGT TTT ACA CTG GTG ACC ACA TTT GCG TTT TCT TTG ATT TTT TCT GTA         162
Cys Phe Thr Leu Val Thr Thr Phe Ala Phe Ser Leu Ile Phe Ser Val
             10              15              20

AGC GCT TTA GCG GGG AGT GTG TTC TGG GAA CCA TTA AGT TAT TTT AAT         210
Ser Ala Leu Ala Gly Ser Val Phe Trp Glu Pro Leu Ser Tyr Phe Asn
             25              30              35

CCG AGT ACA TGG GAA AAG GCA GAT GGG TAT TCC AAT GGG GGG GTG TTC         258
Pro Ser Thr Trp Glu Lys Ala Asp Gly Tyr Ser Asn Gly Gly Val Phe
             40              45              50

AAT TGC ACA TGG CGT GCC AAC AAT GTT AAT TTT ACG AAT GAT GGA AAG         306
Asn Cys Thr Trp Arg Ala Asn Asn Val Asn Phe Thr Asn Asp Gly Lys
         55              60              65

CTC AAG CTG GGC TTA ACG AGT TCT GCG TAC AAC AAA TTT GAC TGC GCG         354
Leu Lys Leu Gly Leu Thr Ser Ser Ala Tyr Asn Lys Phe Asp Cys Ala
 70              75              80              85

GAG TAC CGA TCA ACG AAC ATT TAC GGA TAC GGC CTG TAC GAG GTC AGT         402
Glu Tyr Arg Ser Thr Asn Ile Tyr Gly Tyr Gly Leu Tyr Glu Val Ser
             90              95             100

ATG AAG CCA GCC AAA AAT ACA GGA ATT GTC TCA TCC TTT TTC ACG TAT         450
Met Lys Pro Ala Lys Asn Thr Gly Ile Val Ser Ser Phe Phe Thr Tyr
             105             110             115

ACA GGA CCT GCT CAT GGC ACA CAA TGG GAT GAA ATA GAT ATC GAA TTT         498
Thr Gly Pro Ala His Gly Thr Gln Trp Asp Glu Ile Asp Ile Glu Phe
         120             125             130

TTG GGA AAA GAC ACA ACG AAG GTT CAA TTT AAC TAT TAT ACA AAT GGC         546
Leu Gly Lys Asp Thr Thr Lys Val Gln Phe Asn Tyr Tyr Thr Asn Gly
 135             140             145

GCA GGA AAC CAT GAG AAG TTC GCG GAT CTC GGA TTT GAT GCA GCC AAT         594
Ala Gly Asn His Glu Lys Phe Ala Asp Leu Gly Phe Asp Ala Ala Asn
150              155             160             165

GCC TAT CAT ACG TAT GCG TTC GAT TGG CAG CCA AAC TCT ATT AAA TGG         642
Ala Tyr His Thr Tyr Ala Phe Asp Trp Gln Pro Asn Ser Ile Lys Trp
             170             175             180

TAT GTC GAT GGG CAA TTA AAA CAT ACT GCA ACA ACC CAA ATA CCG GCA         690
Tyr Val Asp Gly Gln Leu Lys His Thr Ala Thr Thr Gln Ile Pro Ala
             185             190             195

GCG CCG GGG AAA ATC ATG ATG AAT TTG TGG AAT GGT ACG GGT GTT GAT         738
Ala Pro Gly Lys Ile Met Met Asn Leu Trp Asn Gly Thr Gly Val Asp
             200             205             210

GAT TGG CTC GGT TCC TAC AAT GGC GTA AAT CCG ATA TAC GCT CAT TAC         786
Asp Trp Leu Gly Ser Tyr Asn Gly Val Asn Pro Ile Tyr Ala His Tyr
             215             220             225

GAC TGG ATG CGC TAT AGA AAA AAA TAATGTACAG AAAAGGATTT CGCTGGCGGA        840
Asp Trp Met Arg Tyr Arg Lys Lys
230             235

ATCCTTTTTT GATTAAAACG AAATAATCCC NNNNNNNNNN NNNNNNNNNN NNNNNNNNNN       900

NNNNNNNNNN NNNNNNNNNN NNNNNNNNNN NNNNNNNNNN NNNNNNNNNN NNNNNNNNNN       960

NNNNNNNNNN NNNNNNNNNN NNNNNNNNNN NNNNNNNNNN NNNNNNNNNN NNNNNNNNNN      1020

NNNNNNNNNN NNNNNNNNNN NNNNNNNNNN NNNNNNNNNN NNNNNNNNNN NNNNNNNNNN      1080

NNNNNNNNNN NNNNNNNNNN NNNNNNNNNN NNNNNNNNNN NNNNNNNNNN NNNNNNNNNN      1140
```

| | | | | |
|---|---|---|---|---|
| NNNNNNNNNN NNNNNNNNNN NNNNNNNNNN NNNNNNNNNN NNNNNNNNNN NNNNNNNNNN | 1200 |
| NNNNNNNNNN NNNNNNNNNN NNNNNNNNNN NNNNNNNNNN NNNNNNNNNN NNNNNNNNNN | 1260 |
| NNNNNNNNNN NNNNNNNNNN NNNNNNNNNN NNNNNNNNNN NNNNNNNNNN NNNNNNNNNN | 1320 |
| NNNNNNNNNN NNNNNNNNNN NNNNNNNNNN NNNNNNNNNN NNNNNNNNNN NNNNNNNNNN | 1380 |
| NNNNNNNNNN NNNNNNNNNN NNNNNNNNNN NNNNNNNNNN NNNNNNNNNN NNNNNNNNNN | 1440 |
| NNNNNNNNNN NNNNNNNNNN NNNNNNNNNN NNNNNNNNNN NNNNNNNNNN NNNNNNNNNN | 1500 |
| NNNNNNNNNN NNNNNNNNNN NNNNNNNNNN NNNNNNNNNN NNNNNNNNNN NNNNNNNNNN | 1560 |
| NNNNNNNNNN NNNNNNNNNN NNNNNNNNNN NNNNNNNNNN NNNNNNNNNN NNNNNNNNNN | 1620 |
| NNNNNNNNNN NNNNNNNNNN NNNNNNNNNN NNNNNNNNNN NNNNNNNNNN NNNNNNNNNN | 1680 |
| NNNNNNNNNN NNNNNNNNNN NNNNNNNNNN NNNNNNNNNN NNNNNNNNNN NNNNNNNNNN | 1740 |
| NNNNNNNNNN NNNNNNNNNN NNNNNNNNNN NNNNNNNNNN NNNNNNNNNN NNNNNNNNNN | 1800 |
| NNNNNNNNNN NNNNNNNNNN NNNNNNNNNN NNNNNNNNNN NNNNNNNNNN NNNNNNNNNN | 1860 |
| NNNNNNNNNN NNNNNNNNNN NNNNNNNNNN NNNNNNNNNN NNNNNNNNNN NNNNNNNNNN | 1920 |
| NNNNNNNNNN NNNNNNNNNN NNNNNNNNNN NNNNNNNNNN NNNNNNNNNN NNNNNNNNNN | 1980 |
| NNNNNNNNNN NNNNNNNNNN NNNNNNNNNN NNNNNNNNNN NNNNNNNNNN NNNNNNNNNN | 2040 |
| NNNNNNNNNN NNNNNNNNNN NNNNNNNNNN NNNNNNNNNN NNNNNNNNNN NNNNNNNNNN | 2100 |
| NNNNNNNNNN NNNNNNNNNN NNNNNNNNNN NNNNNNNNNN NNNNNNNNNN NNNNNNNNNN | 2160 |
| NNNNNNNNNN NNNNNNNNNN NNNNNNNNNN NNNNNNNNNN NNNNNNNNNN NNNNNNNNNN | 2220 |
| NNNNNNNNNN NNNNNNNNNN NNNNNNNNNN NNNNNNNNNN NNNNNNNNNN NNNNNNNNNN | 2280 |
| NNNNNNNNNN NNNNAGATCT | 2300 |

( 2 ) INFORMATION FOR SEQ ID NO:4:

( i ) SEQUENCE CHARACTERISTICS:
        ( A ) LENGTH: 237 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Lys Lys Ser Cys Phe Thr Leu Val Thr Thr Phe Ala Phe Ser
 1               5                  10                  15

Leu Ile Phe Ser Val Ser Ala Leu Ala Gly Ser Val Phe Trp Glu Pro
            20                  25                  30

Leu Ser Tyr Phe Asn Pro Ser Thr Trp Glu Lys Ala Asp Gly Tyr Ser
        35                  40                  45

Asn Gly Gly Val Phe Asn Cys Thr Trp Arg Ala Asn Asn Val Asn Phe
    50                  55                  60

Thr Asn Asp Gly Lys Leu Lys Leu Gly Leu Thr Ser Ser Ala Tyr Asn
65                  70                  75                  80

Lys Phe Asp Cys Ala Glu Tyr Arg Ser Thr Asn Ile Tyr Gly Tyr Gly
                85                  90                  95

Leu Tyr Glu Val Ser Met Lys Pro Ala Lys Asn Thr Gly Ile Val Ser
                100                 105                 110

Ser Phe Phe Thr Tyr Thr Gly Pro Ala His Gly Thr Gln Trp Asp Glu
            115                 120                 125

Ile Asp Ile Glu Phe Leu Gly Lys Asp Thr Thr Lys Val Gln Phe Asn
    130                 135                 140
```

| | | | | | | | | | | | | | | | |
|---|---|---|---|---|---|---|---|---|---|---|---|---|---|---|---|
| Tyr 145 | Tyr | Thr | Asn | Gly | Ala 150 | Gly | Asn | His | Glu | Lys 155 | Phe | Ala | Asp | Leu | Gly 160 |
| Phe | Asp | Ala | Ala | Asn 165 | Ala | Tyr | His | Thr | Tyr 170 | Ala | Phe | Asp | Trp | Gln 175 | Pro |
| Asn | Ser | Ile | Lys 180 | Trp | Tyr | Val | Asp | Gly 185 | Gln | Leu | Lys | His | Thr 190 | Ala | Thr |
| Thr | Gln | Ile 195 | Pro | Ala | Ala | Pro | Gly 200 | Lys | Ile | Met | Met | Asn 205 | Leu | Trp | Asn |
| Gly | Thr 210 | Gly | Val | Asp | Asp | Trp 215 | Leu | Gly | Ser | Tyr | Asn 220 | Gly | Val | Asn | Pro |
| Ile 225 | Tyr | Ala | His | Tyr | Asp 230 | Trp | Met | Arg | Tyr | Arg 235 | Lys | Lys | | | |

We claim:

1. A thermostable hybrid (1,3-1,4)-β-glucanase of the general formula

A–M where A is a polypeptide consisting of a 5 to 107 amino acid sequence which is at least 75% identical to the amino acid sequence of the N-terminal part of the *Bacillus amyloliquefaciens* (1,3-1,4)-β-glucanase and M is a polypeptide consisting of a 107 to 200 amino acid sequence which is at least 75% identical to the amino acid sequence of the C-terminal part of the *Bacillus macerans* (1,3-1,4)-β -glucanase said hybrid (1,3-1,4)-β-glucanase retaining at least 50% of its activity after 10 minutes or more of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans, the hybrid (1,3-1,4)-β-glucanase being more thermostable than any of the glucanases encoded by the parental (1,3-1,4)-β-glucanase genes.

2. A thermostable (1,3-1,4)-βglucanase according to claim 1 which retains at least 50% of its activity after 10 minutes of incubation in 10 mM CaCl$_2$, 40 mM Na-acetate at pH 6.0 and 70° C., the incubated solution having a concentration range from 0.3 to 1 mg (1,3-1,4)-β-glucanase per ml, the activity of the (1,3-1,4)-β-glucanase being understood as the ability of the enzyme to hydrolyze β-glycosidic linkages in (1,3-1,4)-β-glucans.

3. A thermostable (1,3-1,4)-β-glucanase according to claim 1 which retains at least 50% of its activity after 15 minutes of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans.

4. A thermostable (1,3-1,4)-β-glucanase according to claim 3 which retains at least 50% of its activity after 15 minutes of incubation in 10 mM CaCl$_2$, 40 mM Na-acetate at pH 6.0 and 70° C., the incubated solution having a concentration range from 0.3 mg to 1 mg (1,3-1,4)-β-glucanase per ml, the activity of the (1,3-1,4)-β-glucanase being understood as the ability of the enzyme to hydrolyze β-glycosidic linkages in (1,3-1,4)-β-glucans.

5. A thermostable (1,3-1,4)-β-glucanase according to claim 1 which retains at least 50% of its activity after 18 minutes of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3 -1,4)-β-glucans.

6. A thermostable (1,3-1,4)-β-glucanase according to claim 5 which retains at least 50% of its activity after 10 minutes of incubation in 10 mM CaCl$_2$, 40 mM Na-acetate at pH 6.0 and 70° C., the incubated solution having a concentration range from 0.3 mg to 1 mg (1,3-1,4)-β-glucanase per ml, the activity of the (1,3-1,4)-β-glucanase being understood as the ability of the enzyme to hydrolyze β-glycosidic linkages in (1,3-1,4)-β-glucans.

7. A thermostable (1,3-1,4)-β-glucanase according to claim 1 which retains at least 85% of its activity after 30 minutes of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3 -1,4)-β-glucans.

8. A thermostable (1,3-1,4)-β-glucanase according to claim 7 which retains at least 85% of its activity after 60 minutes of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3 -1,4)-β-glucans.

9. A thermostable (1,3-1,4)-β-glucanase according to claim 7 which retains at least 85% of its activity after 30 minutes of incubation in 5–10 mM CaCl$_2$, 20–40 mM Na-acetate at a pH of 4.1 and at a temperature of 65° C., the incubated solution having an enzyme concentration of 0.1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans.

10. A thermostable (1,3-1,4)-β-glucanase according to claim 9 which retains at least 90% of its activity.

11. A thermostable (1,3-1,4)-β-glucanase according to claim 7 which retains at least 85% of its activity after 30 minutes of incubation in 5–10 mM CaCl$_2$, 20–40 mM Na-acetate at a pH of 6.0 and at a temperature of 70° C., the incubated solution having an enzyme concentration of 0.1 mg (1,3-1,4)-β-glucanase per ml.

12. A thermostable (1,3-1,4)-β-glucanase according to claim 11 which retains at least 90% of its activity after 30 minutes of incubation.

13. A thermostable (1,3-1,4)-β-glucanase according to claim 11 which retains at least 85% of its activity after 60 minutes of incubation.

14. A thermostable (1,3-1,4)-β-glucanase according to claim 1 which after 10 minutes of incubation at 65° C. and at pH 6.0 in crude cell extracts has a relative β-glucanase activity of at least 100%.

15. A thermostable (1,3-1,4)-β-glucanase according to claim 14 which after 10 minutes of incubation at 65° C. and at pH 6.0 in crude cell extracts has a relative β-glucanase activity of at least 110%.

16. A thermostable (1,3-1,4)-β-glucanase according to claim 15 which after 10 minutes of incubation at 65° C. and at pH 6.0 in crude cell extracts has a relative β-glucanase activity of at least 120%.

17. A thermostable (1,3-1,4)-β-glucanase according to claim 1 where A is a polypeptide consisting of 16 amino acids which are at least 75% identical to the amino acid residues of the N-terminal part of the *Bacillus amyloliquefaciens* (1,3-1,4)-β-glucanase as given in Table I.

18. A thermostable (1,3-1,4)-β-glucanase according to claim 1 where A is a polypeptide consisting of 36 amino acids which are at least 75% identical to the amino acid residues of the N-terminal part of the *Bacillus amyloliquefaciens* (1,3-1,4)-β-glucanase as given in Table I.

19. A thermostable (1,3-1,4)-β-glucanase according to claim 1 where A is a polypeptide consisting of 78 amino acids which are at least 75% identical to the amino acid residues of the N-terminal part of the *Bacillus amyloliquefaciens* (1,3-1,4)-β-glucanase as given in Table I.

20. A thermostable (1,3-1,4)-β-glucanase according to claim 1 where A is a polypeptide consisting of 107 amino acids which are at least 75% identical to the amino acid residues of the N-terminal part of the *Bacillus amyloliquefaciens* (1,3-1,4)-β-glucanase as given in Table I.

21. A thermostable (1,3-1,4)-β-glucanase according to claim 1 which has a signal peptide linked to the N-terminal end of the enzyme.

22. A thermostable (1,3-1,4)-β-glucanase according to claim 21 which has a signal peptide derived from a Saccharomyces species.

23. A thermostable (1,3-1,4)-β-glucanase according to claim 22 which has a signal peptide which is the signal peptide from yeast α-factor, yeast acid phosphatase or yeast invertase.

24. A thermostable (1,3-1,4)-β-glucanase according to claim 21 which has a signal peptide which is at least 75% identical to the signal peptide of *Bacillus amyloliquefaciens* at the amino acid level.

25. A thermostable (1,3-1,4)-β-glucanase according to claim 1 which comprises the following amino acid sequence (amino acid residues 26–289 of SEQ ID NO: 2)

Gln—Thr—Gly—Gly—Ser—Phe—Phe—Glu—Pro—Phe—Asn—Ser—Tyr—Asn—Ser—Gly—Leu—

Trp—Gln—Lys—Ala—Asp—Gly—Tyr—Ser—Asn—Gly—Asp—Met—Phe—Asn—Cys—Thr—Trp—

Arg—Ala—Asn—Asn—Val—Ser—Met—Thr—Ser—Leu—Gly—Glu—Met—Arg—Leu—Ala—Leu—

Thr—Ser—Pro—Ser—Tyr—Asn—Lys—Phe—Asp—Cys—Gly—Glu—Ans—Arg—Ser—Val—Gln—

Thr—Tyr—Gly—Tyr—Gly—Leu—Tyr—Glu—Val—Arg—Met—Lys—Pro—Ala—Lys—Asn—Thr—

Gly—Ile—Val—Ser—Ser—Phe—Phe—Thr—Tyr—Thr—Gly—Pro—Thr—Glu—Gly—Thr—Pro—

Trp—Asp—Glu—Ile—Asp—Ile—Glu—Phe—Leu—Gly—Lys—Asp—Thr—Thr—Lys—Val—Gln—

Phe—Asn—Tyr—Tyr—Thr—Asn—Gly—Val—Gly—Gly—His—Glu—Lys—Val—Ile—Ser—Leu—

Gly—Phe—Asp—Ala—Ser—Lys—Gly—Phe—His—Thr—Tyr—Ala—Phe—Asp—Trp—Gln—Pro—

Gly—Tyr—Ile—Lys—Trp—Tyr—Val—Asp—Gly—Val—Leu—Lys—His—Thr—Ala—Thr—Ala—

Asn—Ile—Pro—Ser—Thr—Pro—Gly—Lys—Ile—Met—Met—Asn—Leu—Trp—Asn—Gly—Thr—

Gly—Val—Asp—Asp—Trp—Leu—Gly—Ser—Tyr—Asn—Gly—Ala—Asn—Pro—Leu—Tyr—Ala—

Glu—Tyr—Asp—Trp—Val—Lys—Tyr—Thr—Ser—Asn or analogues thereof.

26. A thermostable (1,3-1,4)-β-glucanase according to claim 1 which comprises the following amino acid sequence: (SEQ I.D. NO: 2)

Met—Lys—Arg—Val—Leu—Leu—Ile—Leu—Val—Thr—Gly—Leu—Phe—Met—Ser—Leu—Cys—

Gly—Ile—Thr—Ser—Ser—Val—Ser—Ala—Gln—Thr—Gly—Gly—Ser—Phe—Phe—Glu—Pro—

Phe—Asn—Ser—Tyr—Asn—Ser—Gly—Leu—Trp—Gln—Lys—Ala—Asp—Gly—Tyr—Ser—Asn—

Gly—Asp—Met—Phe—Asn—Cys—Thr—Trp—Arg—Ala—Asn—Asn—Val—Ser—Met—Thr—Ser—

-continued

Leu—Gly—Glu—Met—Arg—Leu—Ala—Leu—Thr—Ser—Pro—Ser—Tyr—Asn—Lys—Phe—Asp—
Cys—Gly—Glu—Asn—Arg—Ser—Val—Gln—Thr—Tyr—Gly—Tyr—Gly—Leu—Tyr—Glu—Val—
Arg—Met—Lys—Pro—Ala—Lys—Asn—Thr—Gly—Ile—Val—Ser—Ser—Phe—Phe—Thr—Tyr—
Thr—Gly—Pro—Thr—Glu—Gly—Thr—Pro—Trp—Asp—Glu—Ile—Asp—Ile—Glu—Phe—Leu—
Gly—Lys—Asp—Thr—Thr—Lys—Val—Gln—Phe—Asn—Tyr—Tyr—Thr—Asn—Gly—Val—Gly—
Gly—His—Glu—Lys—Val—Ile—Ser—Leu—Gly—Phe—Asp—Ala—Ser—Lys—Gly—Phe—His—
Thr—Tyr—Ala—Phe—Asp—Trp—Gln—Pro—Gly—Tyr—Ile—Lys—Trp—Tyr—Val—Asp—Gly—
Val—Leu—Lys—His—Thr—Ala—Thr—Ala—Asn—Ile—Pro—Ser—Thr—Pro—Gly—Lys—Ile—
Met—Met—Asn—Leu—Trp—Asn—Gly—Thr—Gly—Val—Asp—Asp—Trp—Leu—Gly—Ser—Tyr—
Asn—Gly—Ala—Asn—Pro—Leu—Tyr—Ala—Glu—Tyr—Asp—Trp—Val—Lys—Tyr—Thr—Ser—
Asn or analogues thereof.

27. A DNA fragment comprising a nucleotide sequence encoding the thermostable (1,3-1,4)-β-glucanase as defined in claim 1.

28. A DNA fragment according to claim 27 which comprises the following nucleotide sequence: (SEQ ID NO: 1)

```
                    30                                              60
GAATTCAACG AAGAATCGCT GCACTATTAT CGATTCGTCA CCCACTTAAA GTTTTTCGAC
                    90                                             120
CAGCGTCTTT TTAACGGCAC ACACATGGAA AGCCAGGACG ATTTTTTACT GGAGACAGTG
                   150                                             180
AAAGAAAAGT ATCATCAGGC GTATAAATGC ACGAAGAATA TCCATACCTA CATTGAGAAA
                   210                                             240
GAGTATGGGC ATAAGCTCAC CAGTGACGAG CTGCTGTATT TAACGATTCA CATAGAAAGG
                   270                                             300
GTAGTCAAAC AAGTATAATG AAAGCGCTTT CCTCGTATTA ATTGTTTCTT CCATTCATAT
                   330                                             360
ATAGGATTGT TACGGATAAA GCAGGCAAAA CCTATCTGTC TGTGCTGATG GTAGTTTAGG
                   390                                             420
TTTGTATTTT TAACAGAAGG ATTATCATTA TTTCGACCGA TGTTCCCTTT GAAAAGGATC
                   450                                             480
ATGTATGATC AATAAAGAAA GCGTGTTCAA AAAAGGGGGA ATGCTAACAT GAAACGAGTG
                   510                                             540
TTGCTAATTC TTGTCACCGG ATTGTTTATG AGTTTGTGTG GGATCACTTC TAGTGTTTCG
                   570                                             600
GCTCAAACAG GCGGATCGTT TTTTGAACCT TTTAACAGCT ATAACTCCGG GTTATGGCAA
                   630                                             660
AAAGCTGATG GTTACTCAAA TGGAGATATG TTTAACTGCA CTTGGCGTGC TAATAACGTC
                   690                                             720
TCTATGACGT CATTAGGTGA AATGCGTTTG GCGCTGACAA GTCCGTCTTA TAACAAGTTT
                   750                                             780
GACTGCGGGG AAAACCGCTC GGTTCAAACA TATGGCTATG GACTTTATGA AGTCAGAATG
                   810                                             840
AAACCGGCTA AAAACACAGG GATTGTTTCA TCGTTCTTCA CTTATACAGG TCCAACGGAG
                   870                                             900
GGGACTCCTT GGGATGAGAT TGATATCGAA TTTCTAGGAA AAGACACGAC AAAAGTGCAG
```

-continued

```
                930                                              960
TTTAACTATT ATACCAATGG GGTTGGCGGT CATGAAAAGG TTATCTCTCT TGGCTTTGAT 990                                             1020
GCATCAAAGG GCTTCCATAC CTATGCTTTC GATTGGCAGC CAGGGTATAT TAAATGGTAT 1050                                             1080
GTAGACGGTG TTTTGAAACA TACCGCCACC GCGAATATTC CGAGTACGCC AGGCAAAATT 1110                                             1140
ATGATGAATC TATGGAACGG AACCGGAGTG GATGACTGGT TAGGTTCTTA TAATGGAGCG 1170                                             1200
AATCCGTTGT ACGCTGAATA TGACTGGGTA AAATATACGA GCAATTAATA TGATTGCAGC

1230
TGGGCATGAG CTTTTTAGTC CACTCCAGGC ATGCAAGCTT
```

29. A method for producing a thermostable (1,3-1,4)-β-glucanase of the general formula

A–M where A is a polypeptide consisting of a 5 to 107 amino acid sequence which is at least 75% identical to the amino acid sequence of the N-terminal part of the *Bacillus amyloliquefaciens* (1,3-1,4)-β-glucanase and M is a polypeptide consisting of a 107 to 200 amino acid sequence which is at least 75% identical to the amino acid sequence of the C-terminal part of the *Bacillus macerans* (1,3-1,4)-β-glucanase said hybrid (1,3-1,4)-β-glucanase retaining at least 50% of its activity after 10 minutes or more of incubation in 5–10 mM $CaCl_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans, the hybrid (1,3-1,4)-β-glucanase being more thermostable than any of the glucanases encoded by the parental (1,3-1,4)-β-glucanase genes comprising cultivating a microorganism in which a DNA fragment as defined in claim 27 has been introduced in such a way that the microorganism is capable of expressing the thermostable (1,3-1,4)-β-glucanase, the cultivation being performed under conditions leading to production of the thermostable (1,3-1,4)-β-glucanase and recovering the (1,3-1,4)-β-glucanase from the culture.

30. A method according to claim 29 wherein the microorganism is a bacterium.

31. A method according to claim 30 wherein the bacterium is a gram-negative bacterium.

32. A method according to claim 31 wherein the gram-negative bacterium is an *E. coli* strain.

33. A method according to claim 32 wherein the *E. coli* strain is the *E. coli* strain harboring plasmid pUC13-H1, deposited in Deutsche Sammlung von Mikroorganismen under Accession No. DSM 5461.

34. A method according to claim 32 wherein the *E. coli* strain is the *E. coli* strain harboring plasmid pTZ19R-H3, deposited in Deutsche Sammlung von Mikroorganismen under Accession No. DSM 5790.

35. A method according to claim 32 wherein the *E. coli* strain is the *E. coli* strain harboring plasmid pTZ19R-H4, deposited in Deutsche Sammlung von Mikroorganismen under Accession No. DSM 5791.

36. A method according to claim 32 wherein the *E. coli* strain is the *E. coli* strain harboring plasmid pTZ19R-H5, deposited in Deutsche Sammlung von Mikroorganismen under Accession No. DSM 5792.

37. A method according to claim 32 wherein the *E. coli* strain is the *E. coli* strain harboring plasmid pTZ19R-H6, deposited in Deutsche Sammlung von Mikroorganismen under Accession No. DSM 5793.

38. A method according to claim 29 wherein the microorganism is a yeast.

39. A method according to claim 38 wherein the yeast is a Saccharomyces species.

40. A method according to claim 39 wherein the Saccharomyces species is *Saccharomyces cerevisiae*.

41. A eukaryotic or prokaryotic organism that is transformed with and is capable of expressing the DNA fragment as defined in claim 27.

42. An organism according to claim 41 which is a microorganism.

43. A microorganism according to claim 42 which is a bacterium.

44. A bacterium according to claim 43 which is a gram-negative bacterium.

45. A bacterium according to claim 44 which is an *E. coli* strain.

46. A bacterium according to claim 45 which is of the *E. coli* strain harboring plasmid pUC13-H1 and which has been deposited in Deutsche Sammlung von Mikroorganismen under Accession No. DSM 5461, and mutants and variants thereof.

47. A bacterium according to claim 45 that is of the *E. coli* strain harboring plasmid pTZ19R-H3, which strain has been deposited in Deutsche Sammlung von Mikroorganismen under Accession No. DSM 5790, and mutants and variants thereof.

48. A bacterium according to claim 45 that is of the *E. coli* strain harboring plasmid pTZ19R-H4, which strain has been deposited in Deutsche Sammlung von Mikroorganismen under Accession No. DSM 5791, and mutants and variants thereof.

49. A bacterium according to claim 45 that is of the *E. coli* strain harboring plasmid pTZ19R-H5, which strain has been deposited in Deutsche Sammlung von Mikroorganismen under Accession No. DSM 5792, and mutants and variants thereof.

50. A bacterium according to claim 45 that is of the *E. coli* strain harboring plasmid pTZ19R-H6, which strain has been deposited in Deutsche Sammlung von Mikroorganismen under Accession No. DSM 5793, and mutants and variants thereof.

51. A microorganism according to claim 42 which is a yeast.

52. A yeast according to claim 51 which is a Saccharomyces species.

53. A Saccharomyces species according to claim 52 which is *Saccharomyces cerevisiae*.

54. An organism according to claim 41 which is a plant.

55. A plant according to claim 54 which is oat, barley, rye, wheat, rice or maize.

56. A method of degrading (1,3-1,4)-β-glucans in a substrate comprising subjecting the substrate to the action of an effective amount of a thermostable (1,3-1,4)-β-glucanase as defined in claim 1 for a period of time at a temperature of 65° C. or higher, the amount of (1,3-1,4)-β-glucanase being at the most 200 µg pr. kg of substrate.

57. A method according to claim 56 wherein the substrate comprises unmodified raw grains or parts thereof from barley or oats or other grains.

58. A method according to claim 56 in which the substrate comprising (1,3-1,4)-β-glucans is mixed with a second substrate originating from maize, rice or wheat comprising a thermostable (1,3-1,4)-β-glucanase of the general formula

A–M where A is a polypeptide consisting of a 5 to 107 amino acid sequence which is at least 75% identical to the amino acid sequence of the N-terminal part of the *Bacillus amyloliquefaciens* (1,3-1,4)-β-glucanase and M is a polypeptide consisting of a 107 to 200 amino acid sequence which is at least 75% identical to the amino acid sequence of the C-terminal part of the *Bacillus macerans* (1,3-1,4)-β -glucanase said hybrid (1,3-1,4)-β-glucanase retaining at least 50% of its activity after 10 minutes or more of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans, the hybrid (1,3-1,4)-β-glucanase being more thermostable than any of the glucanases encoded by the parental (1,3-1,4)-β-glucanase genes.

59. A method for the production of beer, characterized in that the wort is subjected to treatment with a thermostable (1,3-1,4)-β-glucanase according to claim 1 during mashing at a temperature of 65° C. or higher and a pH between 4 and 5.5.

60. A method according to claim 59 in which the temperature is 70° C. or higher.

61. A method for the production of animal feed comprising β-glucans, characterized in that the feed is supplemented with a thermostable (1,3-1,4)-β-glucanase according to claim 1 in an amount sufficient to obtain a significant degradation of β-glucans in the gastrointestinal tract of an animal fed with the (1,3-1,4)-β-glucanase supplemented feed.

62. A method according to claim 61 wherein the animal feed is pelletized.

63. A method according to claim 56, wherein the amount of (1,3-1,4)-β-glucanase is at the most 50 µg per kg of substrate.

64. A method according to claim 63, wherein the amount of (1,3-1,4)-β-glucanase is at the most 15 µg per kg of substrate.

65. A thermostable (1,3-1,4)-β-glucanase according to claim 1, wherein A is a polypeptide consisting of 5 to 107 amino acids which are at least 90% identical to the amino acid residues of the N-terminal part of the *Bacillus amyloliquefaciens* (1,3 -1,4)-β-glucanase as given in Table I.

66. A thermostable (1,3-1,4)-β-glucanase according to claim 17, wherein A is a polypeptide consisting of 16 amino acids which are at least 90% identical to the amino acid residues of the N-terminal part of the *Bacillus amyloliquefaciens* (1,3-1,4)-β -glucanase as given in Table I.

67. A thermostable (1,3-1,4)-β-glucanase according to claim 18, wherein A is a polypeptide consisting of 36 amino acids which are at least 90% identical to the amino acid residues of the N-terminal part of the *Bacillus amyloliquefaciens* (1,3-1,4)-β -glucanase as given in Table I.

68. A thermostable (1,3-1,4)-β-glucanase according to claim 19, wherein A is a polypeptide consisting of 78 amino acids which are at least 90% identical to the amino acid residues of the N-terminal part of the *Bacillus amyloliquefaciens* (1,3-1,4)-β -glucanase as given in Table I.

69. A thermostable (1,3-1,4)-β-glucanase according to claim 20, wherein A is a polypeptide consisting of 107 amino acids which are at least 90% identical to the amino acid residues of the N-terminal part of the *Bacillus amyloliquefaciens* (1,3 -1,4)-β-glucanase as given in Table I.

70. A method according to claim 61, wherein the feed is supplemented with a thermostable (1,3-1,4)-β-glucanase in an amount sufficient to obtain a significant degradation of β-glucans in the (1,3-1,4)-β-glucanase supplemented feed.

71. A method for producing a thermostable (1,3-1,4)-β-glucanase of the general formula

A–M where A is a polypeptide consisting of a 5 to 107 amino acid sequence which is at least 75% identical to the amino acid sequence of the N-terminal part of the *Bacillus amyloliquefaciens* (1,3-1,4)-β-glucanase and M is a polypeptide consisting of a 107 to 200 amino acid sequence which is at least 75% identical to the amino acid sequence of the C-terminal part of the *Bacillus macerans* (1,3-1,4)-β -glucanase said hybrid (1,3-1,4)-β-glucanase retaining at least 50% of its activity after 10 minutes or more of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans, the hybrid (1,3-1,4)-β-glucanase being more thermostable than any of the glucanases encoded by the parental (1,3-1,4)-β-glucanase genes comprising cultivating a microorganism in which a DNA fragment as defined in claim 28 has been introduced in such a way that the microorganism is capable of expressing the thermostable (1,3-1,4)-β-glucanase, the cultivation being performed under conditions leading to production of the thermostable (1,3-1,4)-β-glucanase and recovering the (1,3-1,4)-β -glucanase from the culture.

72. A thermostable hybrid (1,3-1,4)-β-glucanase of the general formula

A–M where A is a polypeptide consisting of a 16 to 107 amino acid sequence which is at least 75% identical to the amino acid sequence of the N-terminal part of the *Bacillus amyloliquefaciens* (1,3-1,4)-β-glucanase and M is a polypeptide consisting of a 107 to 198 amino acid sequence which is at least 75% identical to the amino acid sequence of the C-terminal part of the *Bacillus macerans* (1,3-1,4)-β-glucanase said hybrid (1,3-1,4)-β-glucanase retaining at least 50% of its activity after 10 minutes or more of incubation in 5–10 mM CaCl$_2$, 20–40 mM Na-acetate at a pH of 6.0 or lower and at a temperature of 65° C. or higher, the incubated solution having an enzyme concentration range from 0.05 mg to 1 mg (1,3-1,4)-β-glucanase per ml, the activity of (1,3-1,4)-β-glucanase being understood as the ability of the enzyme to hydrolyze β-glycosidic linkages in (1,3-1,4)-β-glucans, the hybrid (1,3-1,4)-β-glucanase being more thermostable than any of the glucanases encoded by the parental (1,3-1,4)-β-glucanase genes.

* * * * *